US006630328B2

(12) United States Patent
Quax

(10) Patent No.: US 6,630,328 B2
(45) Date of Patent: *Oct. 7, 2003

(54) INCREASING PRODUCTION OF PROTEINS IN GRAM-POSITIVE MICROORGANISMS

(75) Inventor: Wilhelmus J. Quax, Voorschoten (NL)

(73) Assignee: Genencor International, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/899,482

(22) Filed: Jul. 5, 2001

(65) Prior Publication Data

US 2002/0006641 A1 Jan. 17, 2002

Related U.S. Application Data

(63) Continuation of application No. 09/462,844, filed as application No. PCT/US98/14786 on Jul. 15, 1998, now Pat. No. 6,258,563.

(30) Foreign Application Priority Data

Jul. 15, 1909 (EP) ............................................. 97305344
Jul. 16, 1997 (EP) ............................................. 97305286

(51) Int. Cl.[7] ........................... C12P 21/04; C12N 1/20; C07H 21/04

(52) U.S. Cl. ...................... 435/69.8; 435/6; 435/69.1; 435/71.1; 435/320.1; 435/252.31; 536/23.7

(58) Field of Search .............................. 435/69.8, 69.1, 435/69.3, 320.1, 252.3, 252.31, 5, 6, 71.1; 536/23.1, 23.7

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,816,567 A | 3/1989 | Cabilly et al. |
| 5,945,278 A | * | 8/1999 | Kontinen et al. |
| 6,258,563 B1 | * | 7/2001 | Quax |

FOREIGN PATENT DOCUMENTS

WO    WO 94/19471    9/1994

OTHER PUBLICATIONS

Ausubel et al., Current Protocols in Molecular Biology, John Wiley & Sons, Inc. Ch. 2 and 3, 1987.
Bakhiet et al., "Studies on Transfection and Transformation of Protoplasts of *Bacillus larvae*, *Bacillus subtilis*, and *Bacillus popilliae*," *Applied and Environmental Microbiology*, vol. 49, No. 3, pp. 577–581, Mar. 1985.

Berger and Kimmel, "Guide to Molecular Cloning Techniques," Methods in Enzymology, Academic Press, San Diego, CA, vol. 152, 1987.
Bolhuis et al., "*Bacillus subtilis* can modulate its capacity and specificity for protein secretion through temporarly controlled expression of the sipS gene for signal peptidase I," *Molecular Microbiology*, vol. 22(4), pp. 605–618, 1996.
Chang et al., "High Frequency Transformation of *Bacillus subtilis* Protoplasts by Plasmid DNA," *Molec. Gen. Genet.*, vol. 168, pp. 111–115, 1979.
Coombs, J., Dictionary of Biotechnology, Stockton Press, New York, New York, 1994.
Dieffenbach, C.W. et al., PCR Primer, a Laboratory Manual, Cold Spring Harbor Press, Plainview, NY, pp. 477–508, 1995.
Contente et al., "Marker Rescue Transformation by Linear Plasmid DNA in *Bacillus subtilis*," *Plasmid*, vol. 555–571, 1979.
Evan et al., "Isolation of Monoclonal Antibodies specific for Human c-myc Proto-Oncogene Product," *Molecular and Cellular Biology*, vol. 5, No. 12, pp. 3610–3616, 1985.
Fischer et al., "Introduction of plasmid pC194 into *Bacillus thuringiensis* by protoplast transformation and plasmid transfer," *Archives of Microbiology*, vol. 139, pp. 213–217, 1984.
Haima et al., "Novel plasmid marker rescue transformation system for molecular cloning in *Bacillus subtilis* enabling direc selection of recombinants," *Mol. Gen. Genet.*, vol. 223, pp. 185–191, 1990.
Hampton, R., et al., Serological Methods, a Laboratory Manual, APS Press, St. Paul, MN, 1990.
Harwood and Cutting, ed., Molecular Biological Methods for *Bacillus*, John Wiley & Sons, 1995.
Holubova et al., "Transfer of Liposome–Encapsulated Plasmid DNA to *Bacillus subtilis* Protoplasts and Calcium–Treated *Escherichia coli* Cells," *Folia Microbiol.*, vol. 30, pp. 97–100, 1985.
Jander et al., "Biotinylation In Vivo as a Sensitive Indicator of Protein Secretion and Membrane Protein Insertion," *J. of Bacteriology*, vol. 178, No. 11, pp. 3049–3058, 1996.
Kim et al., "A xylose–inducible *Bacillus subtilis* integration vector and its application," *Gene*, vol. 181, pp. 71–76, 1996.
Kontinen et al., "Mutants of *Bacillus subtilis* Defective in Protein Export," *J. of General Microbiology*, vol. 134, pp. 2333–2344, 1988.

(List continued on next page.)

Primary Examiner—Sean McGarry
Assistant Examiner—Janet Epps-Ford
(74) Attorney, Agent, or Firm—Genencor International, Inc.

(57) ABSTRACT

The present invention relates to secretion in Gram-positive microorganisms. The present invention provides the nucleic acid amino acid sequences for the *Bacillus subtilis* secretion factors SecDF. The present invention also provides improved methods for the secretion of heterologous or homologous proteins in gram-positive microorganisms.

22 Claims, 18 Drawing Sheets

OTHER PUBLICATIONS

Kroll et al., "A Multifunctional Prokaryotic Protein Expression System: Overproduction, Affinity Purification, and Selective Detection," *DNA and Cell Biology*, vol. 12, No. 5, pp. 441–453, 1993.

Kunst et al., "Salt Stress Is an Environmental Signal Affecting Degradative Enzyme Synthesis in *Bacillus subtilis*," *J. of Bacteriology*, vol. 177, No. 9, pp. 2403–2407, 1995.

Kunst et al., "The complete genome sequence of the Gram–positive bacterium *Bacillus subtillis*," *Nature*, vol. 390, pp. 249–256, 1997.

Laemmli, "Cleavage of Structural proteins during the Assembly of the Head of Bacteriophage T4," *Nature*, vol. 227, pp. 680–685,1970.

Maddox et al., "Elevated Serum Levels in Human Pregnancy of a Molecule Immunochemically Similar to Eosinophil Granule Major Basic Protein," *J. Exp. Med.*, 158, pp. 1211–1226, Oct. 1993.

Mann et al., "transformation of *Bacillus spp*.: an Examination of the Transformation of *Bacillus* Protoplast by Plasmids pUB110 and pHV33," *Currents Microbiology*, vol. 13, pp. 191–195, 1986.

McDonald et al., "Plasmid Transformation of *Bacillus sphaericus* 1593," *J. of General Microbiology*, vol. 130, pp, 203–208, 1984.

Miller, Experiments in Molecular Genetics, Cold Spring Harbor Laboratory Press, Cold Spring Harbor, New York, 1982.

Murray et al., "Codon usage in plant genes," Nucleic Acids Research, vol. 17, No. 2, pp. 477–497, 1989.

Palva, Molecular cloning of α–amylase gene from *Bacillus amyloliquefaciens* and its expression in *B. subtilis, Gene*, vol. 19, pp. 81–87, 1982.

Pogliano et al., "Genetic and Molecular Characterization of the *Escherichia coli secD* Operon and Its Products," *J. Bacteriology*, vol. 176, No. 3, pp. 804–814, 1994.

Porath, "Immobilized Metal Ion Affinity Chromatography," *Protein Expression and Purification*, vol. 3, pp. 263–281, 1992.

Reuter et al., "Structure and Organization of *Escherichia coli* Genes Involved in Biosynthesis of the Deazaguanine Derivative Queuine, A Nutrient Factor for Eukaryotes," *J. of Bacteriology*, vol. 173, No. 7, pp. 2256–2264, 1991.

Sambrook, J. et al., Molecular Cloning: A Laboratory Manual, Cold Spring Harbor Press, Cold Spring Harbor, New York, New York, 1989.

Sipos et al., "Predicting the topology of eukaryotic membrane proteins," *Eur. J. Biochemistry*, vol. 213, pp. 1333–1340, 1993.

Smith et al., "Protoplast Transformation in Coryneform Bacteria and Introduction of an α–Amylase Gene from *Bacillus amyloliquefaciens* into *Brevibacterium lactofermentum*," *Applied and Enviromental Microbiology*, vol. 51, No. 3, pp. 634–639, Mar. 1986.

Takkinen et al., "Amino Acid Sequence of α–Amylase from *Bacillus amyloloquefaciens* Deduced from the Nucleotide sequence of the Cloned Gene," *J. of Biological Chemistry*, vol. 258, No. 2, pp. 1007–1013, 1982.

Tjalsma et al., "*Bacillus subtilis* Contains Four Closely Related Type I Signal Peptidases with Overlapping Substrate Specificities," *J. of Biological Chemistry*, vol. 272, No. 41, pp. 25983–25992, 1997.

van Dijl et al., "Non–functional expression of *Escherichia coli* signal peptidase I in *Bacillus subtilis*," *J. of General Microbiology*, vol. 137, pp. 2073–2083, 1991.

van Dijl et al., "Signal peptidase I of *Bacillus subtilis*: patterns of conserved amino acids in prokaryotic and eukaryotic type I signal peptidase," *EMBO Journal*, No. 11, No. 8, pp. 2819–2828, 1992.

Vorobjeva, et al., "Transformation of *Bacillus Megaterium* Protoplasts by Plasmid DNA," *FEMS Microbiology Letters* 7, pp. 261–263, 1980.

Weinrauch et al., "Plasmid Marker Rescue Transformation in *Bacillus subtilis*," *Journal of Bacteriology*, vol. 154, No. 3, pp. 1077–1087, Jun. 1983.

Weinrauch et al., "Plasmid Marker Rescue Transformation Proceeds by Breakage–Reunion in *Bacillus subtilis*," *J. of Bacteriology*, vol. 169, No. 3, pp. 1205–1211, 1987.

Copy of International Search Report.

Bolhuis, A. et al., "SecDF of *Bacillus Subtilis*, a Molecular Siamese Twin Required for the Efficient Secretion of Proteins," Journal od Biological Chemistry, vol. 273, No. 33, pp. 21217–21224, Aug. 14, 1998.

Gardel, C. et al., "The secD locus of *E. coli* codes for two membrane proteins required for protein export," EMBO Journal, vol. 9, No. 10, pp. 3209–3216, 1990.

Suh, J.–W. et al., "Isolation of a secY homologue from *Bacillus subtilis*: evidence for a common protein export pathway in eubacteria," Molecular Microbiology, vol. 4, No. 2, pp. 305–314, Jan. 1, 1990.

* cited by examiner

```
        10                           30
ATGAAAAAAGGACGCTTGATTGCGTTTTTCCTTTTCGTTCTATTGATC
 M  K  K  G  R  L  I  A  F  F  L  F  V  L  L  I 50                           70                         90
GGCACGGGCTTGGGCTACTTTACGAAGCCTGCCGCTAACAATATTACG
 G  T  G  L  G  Y  F  T  K  P  A  A  N  N  I  T 110                          130
TTAGGATTGGATTTGCAAGGCGGATTTGAGGTGCTGTATGATGTACAG
 L  G  L  D  L  Q  G  G  F  E  V  L  Y  D  V  Q 150                          170                         190
CCTGTAAAAAAGGTGACAAAATCACAAAAGACGTTCTGGTCAGCACA
 P  V  K  K  G  D  K  I  T  K  D  V  L  V  S  T 210                         230
GTAGAGGCACTGAACCGCCGGGCCAATGTTCTCGGTGTCAGCGAACCG
 V  E  A  L  N  R  R  A  N  V  L  G  V  S  E  P 250                          270                         2
AACATCCAAATTGAAGGGAATAACCGGATTCGCGTTCAGCTCGCTGGC
 N  I  Q  I  E  G  N  N  R  I  R  V  Q  L  A  G 90                          310                         330
GTGACAAACCAAAACAGAGCGCGTGAAATTTTGGCGACTGAAGCGCAG
 V  T  N  Q  N  R  A  R  E  I  L  A  T  E  A  Q 350                         370
CTTTCTTTCAGAGATGCAAATGATAAGGAACTGTTAAACGGTGCTGAT
 L  S  F  R  D  A  N  D  K  E  L  L  N  G  A  D 390                         410                          430
CTAGTCGAAAACGGCGCTAAACAAACTTATGATAGCACAACAAATGAG
 L  V  E  N  G  A  K  Q  T  Y  D  S  T  T  N  E 450                         470
CCAATTGTCACGATTAAGCTGAAAGACGCTGATAAATTTGGTGAAGTG
 P  I  V  T  I  K  L  K  D  A  D  K  F  G  E  V
```

FIG._1A

```
          490                      510                         5
ACCAAGAAGGTCATGAAAATGGCGCCAAACAACCAGCTTGTCATTTGG
 T  K  K  V  M  K  M  A  P  N  N  Q  L  V  I  W 30                      550                       570
TTGGATTATGATAAAGGTGATTCCTTTAAGAAAGAAGTTCAAAAAGAG
 L  D  Y  D  K  G  D  S  F  K  K  E  V  Q  K  E 590                      610
CATCCTAAATTTGTATCCGCTCCAAATGTAAGTCAGGAACTAAATACA
 H  P  K  F  V  S  A  P  N  V  S  Q  E  L  N  T 630                      650                      670
ACTGATGTAAAAATTGAAGGTCATTTCACAGCTCAAGAAGCGAAAGAT
 T  D  V  K  I  E  G  H  F  T  A  Q  E  A  K  D 690                      710
TTAGCCAGCATTTTAAACGCAGGCGCACTTCCTGTGAAACTGACTGAA
 L  A  S  I  L  N  A  G  A  L  P  V  K  L  T  E 730                     750                         7
AAGTATTCGACATCAGTAGGCGCGCAATTCGGCCAGCAGGCTCTCCAT
 K  Y  S  T  S  V  G  A  Q  F  G  Q  Q  A  L  H 70                      790                       810
GATACGGTGTTTGCCGGTATTGTCGGTATCGCAATTATTTTCTTATTT
 D  T  V  F  A  G  I  V  G  I  A  I  I  F  L  F 830                      850
ATGCTTTTCTATTACCGTCTGCCGGGATTAATCGCGGTGATTACGCTG
 M  L  F  Y  Y  R  L  P  G  L  I  A  V  I  T  L 870                      890                      910
TCTGTTTATATCTACATTACACTCCAGATCTTTGACTGGATGAATGCC
 S  V  Y  I  Y  I  T  L  Q  I  F  D  W  M  N  A 930                      950
GTACTCACGCTTCCGGGAATTGCCGCTCTCATTTTAGGTGTCGGGATG
 V  L  T  L  P  G  I  A  A  L  I  L  G  V  G  M 970                      990                10
GCTGTTGACGCCAACATTATTACCTATGAGCGGATTAAAGAAGAGCTC
 A  V  D  A  N  I  I  T  Y  E  R  I  K  E  E  L
```

FIG._1B

```
       10                  1030                 1050
AAGCTAGGAAAGTCAGTCCGCTCTGCCTTCCGTTCAGGAAACAGACGG
 K  L  G  K  S  V  R  S  A  F  R  S  G  N  R  R 1070                 1090
TCATTTGCGACGATTTTTGACGCGAATATTACAACCATTATTGCAGCG
 S  F  A  T  I  F  D  A  N  I  T  T  I  I  A  A 1110                1130                 1150
GTTGTGCTCTTTATCTTTGGGACAAGCTCTGTTAAAGGGTTTGCGACA
 V  V  L  F  I  F  G  T  S  S  V  K  G  F  A  T 1170                 1190
ATGCTGATCCTATCGATTTTGACAAGCTTTATCACTGCCGTTTTCTTA
 M  L  I  L  S  I  L  T  S  F  I  T  A  V  F  L 1210                1230                   12
TCGAGATTTCTCCTCGCTCTCCTTGTGGAAAGCAGATGGCTTGATCGG
 S  R  F  L  L  A  L  L  V  E  S  R  W  L  D  R 50                  1270                 1290
AAAAAAGGCTGGTTTGGTGTCAATAAGAAACATATCATGGATATTCAG
 K  K  G  W  F  G  V  N  K  K  H  I  M  D  I  Q 1310                 1330
GATACGGATGAAAATACAGAGCCGCATACGCCATTCCAAAAATGGGAT
 D  T  D  E  N  T  E  P  H  T  P  F  Q  K  W  D 1350                1370                 1390
TTCACGAGCAAACGCAAATACTTCTTTATTTTCTCCAGTGCGGTCACG
 F  T  S  K  R  K  Y  F  F  I  F  S  S  A  V  T 1410                 1430
GTTGCCGGGATTATTATCCTGCTTGTGTTCAGGCTGAATCTTGGCATT
 V  A  G  I  I  I  L  L  V  F  R  L  N  L  G  I 1450                 1470            14
GACTTTGCAAGCGGTGCACGGATTGAAGTGCAAAGCGACCATAAGCTG
 D  F  A  S  G  A  R  I  E  V  Q  S  D  H  K  L
```

*FIG._1C*

```
        90                  1510                  1530
ACGACAGAGCAAGTTGAGAAGGATTTTGAATCTCTGGGTATGGACCCT
 T  T  E  Q  V  E  K  D  F  E  S  L  G  M  D  P 1550                  1570
GATACTGTAGTTCTGTCAGGCGAAAAGAGCAATATCGGTGTTGCCCGT
 D  T  V  V  L  S  G  E  K  S  N  I  G  V  A  R 1590                  1610                  1630
TTTGTCGGGGTGCCAGATAAAGAAACCATTGCAAAAGTAAAAACGTAT
 F  V  G  V  P  D  K  E  T  I  A  K  V  K  T  Y 1650                  1670
TTTAAAGACAAATACGGATCTGATCCAAATGTCAGCACAGTTTCACCG
 F  K  D  K  Y  G  S  D  P  N  V  S  T  V  S  P 1690                  1710              17
ACAGTCGGTAAGGAGCTGGCGAGAAATGCGCTGTACGCAGTTGCTATA
 T  V  G  K  E  L  A  R  N  A  L  Y  A  V  A  I 30                  1750                  1770
GCTTCTATTGGCATCATTATTTACGTTTCAATCCGATTCGAATACAAA
 A  S  I  G  I  I  I  Y  V  S  I  R  F  E  Y  K 1790                  1810
ATGGCGATTGCTGCCATCGCCTCATTGCTATATGACGCATTCTTTATC
 M  A  I  A  A  I  A  S  L  L  Y  D  A  F  F  I 1830                  1850                  1870
GTCACGTTCTTCAGTATTACAAGGCTTGAGGTAGATGTTACATTCATC
 V  T  F  F  S  I  T  R  L  E  V  D  V  T  F  I 1890                  1910
GCGGCCATCTTGACGATAATCGGGTATTCCATTAACGATACAATCGTT
 A  A  I  L  T  I  I  G  Y  S  I  N  D  T  I  V 1930                  1950              19
ACATTTGACAGGGTCCGCGAGCATATGAAAAAGCGTAAGCCGAAAACC
 T  F  D  R  V  R  E  H  M  K  K  R  K  P  K  T
```

FIG._1D

```
70                    1990                    2010
TTTGCCGATCTGAACCATATTGTAAACCTGAGCCTGCAGCAAACCTTT
 F  A  D  L  N  H  I  V  N  L  S  L  Q  Q  T  F 2030                    2050
ACACGTTCAATTAACACTGTATTAACCGTTGTGATTGTTGTTGTGACA
 T  R  S  I  N  T  V  L  T  V  V  I  V  V  V  T 2070                    2090                    2110
TTGCTGATCTTTGGAGCATCTTCTATTACTAACTTCTCAATTGCTTTA
 L  L  I  F  G  A  S  S  I  T  N  F  S  I  A  L 2130                    2150
TTGGTCGGGCTGTTAACAGGCGTTTATTCTTCTCTATACATTGCCGCA
 L  V  G  L  L  T  G  V  Y  S  S  L  Y  I  A  A 2170                    2190             22
CAAATTTGGCTTGCATGGAAAGGAAGAGAACTGAAAAAGATTCGGCG
 Q  I  W  L  A  W  K  G  R  E  L  K  K  D  S  A

10
CAATAA
 Q  *
```

FIG._1E

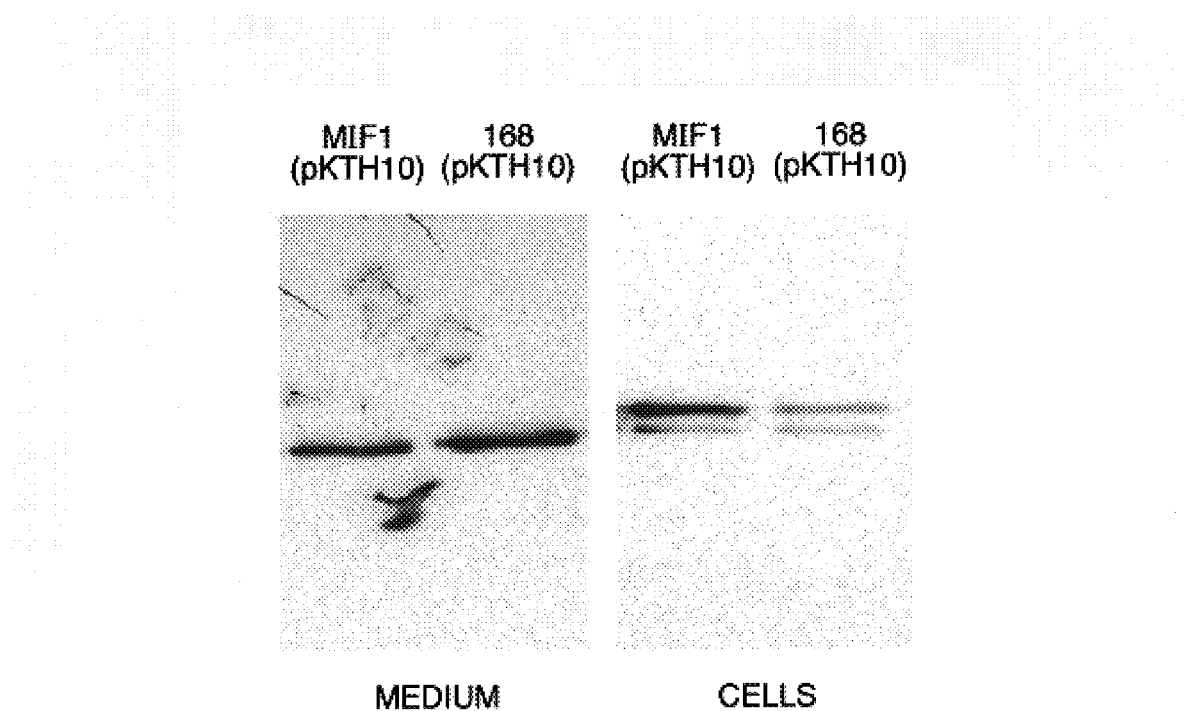
FIG._2
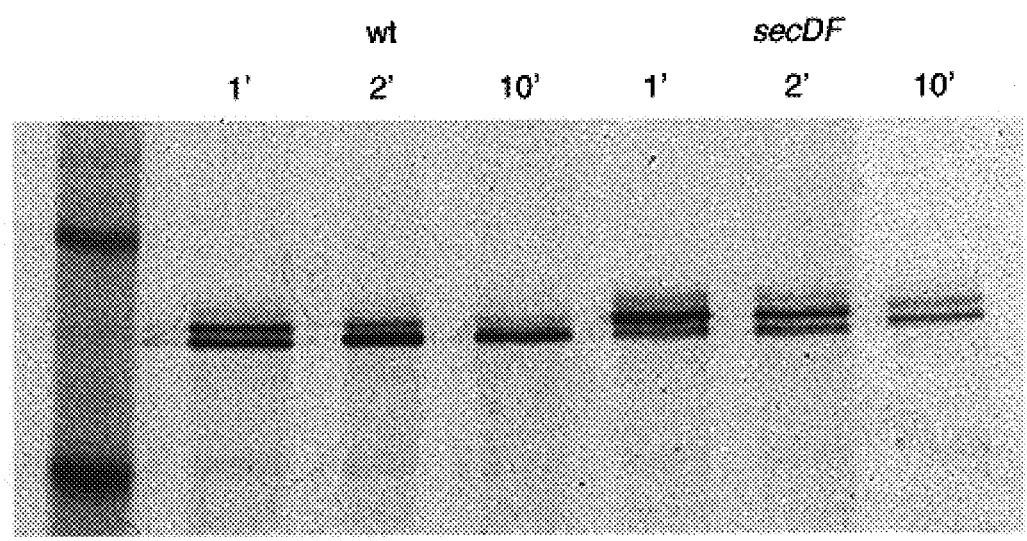
FIG._5A

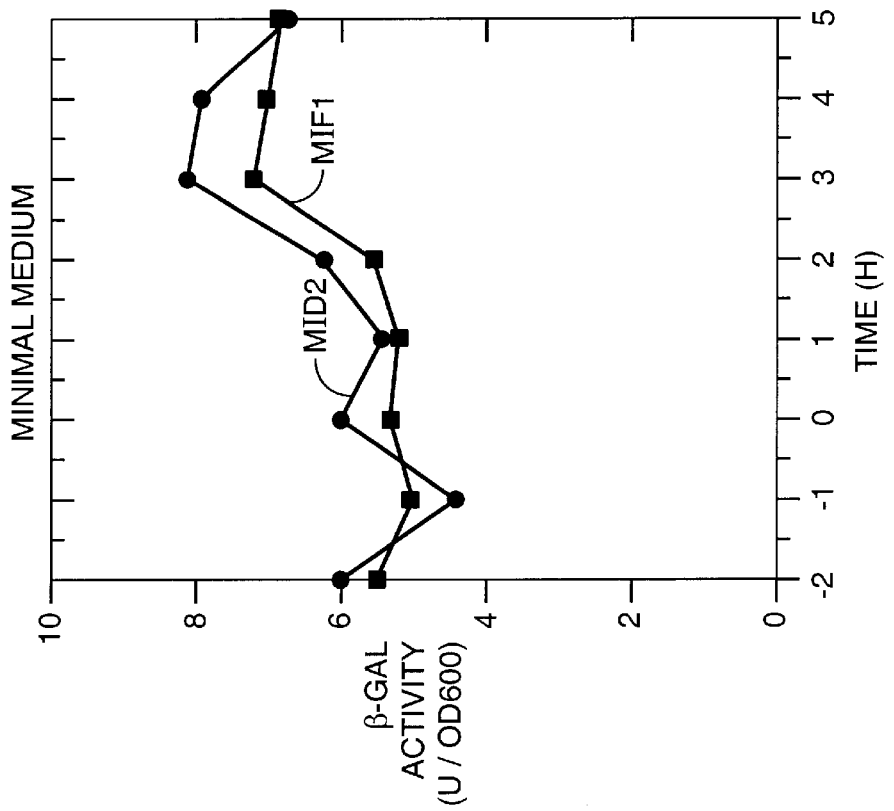
FIG._3B
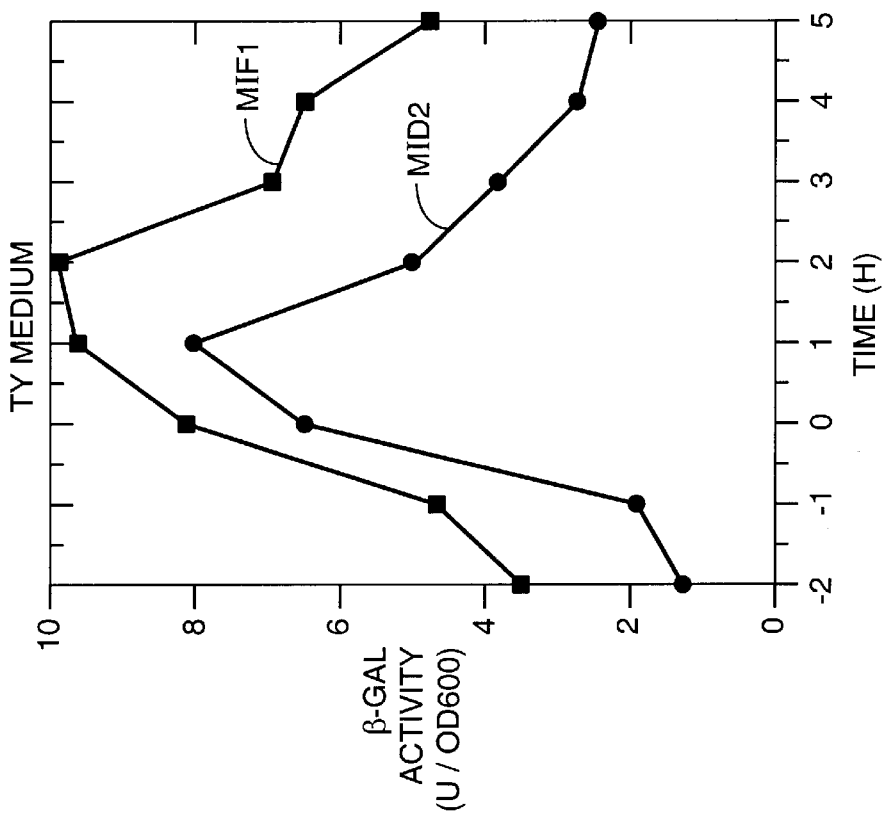
FIG._3A

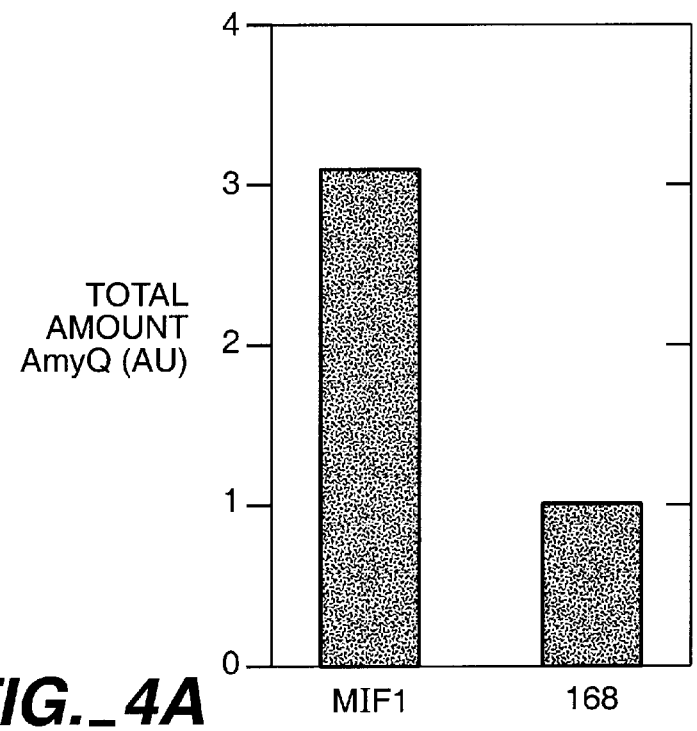
FIG._4A
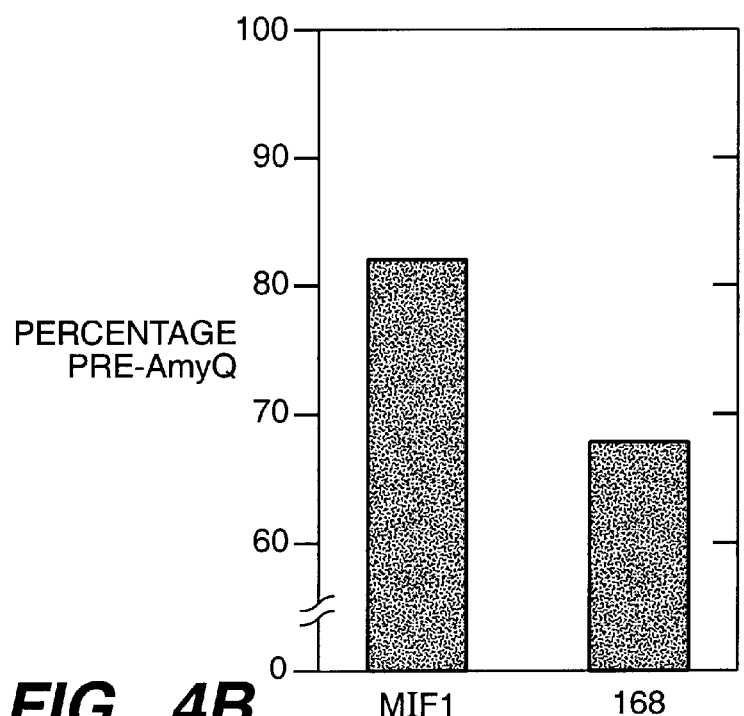
FIG._4B

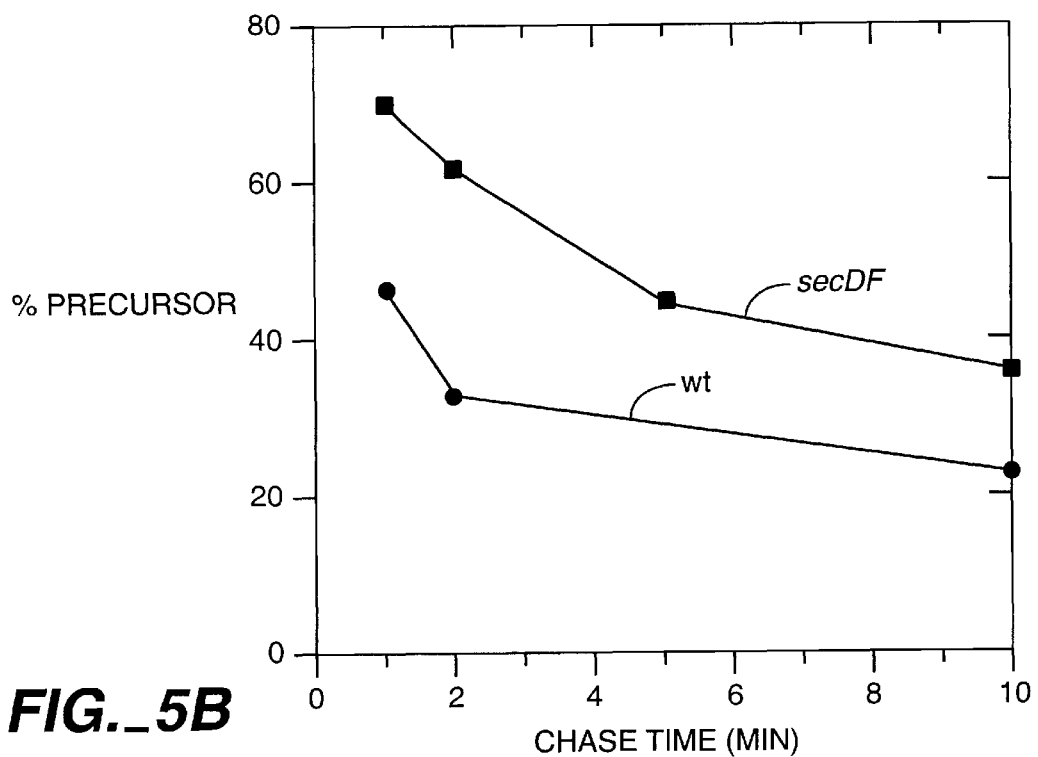
FIG._5B
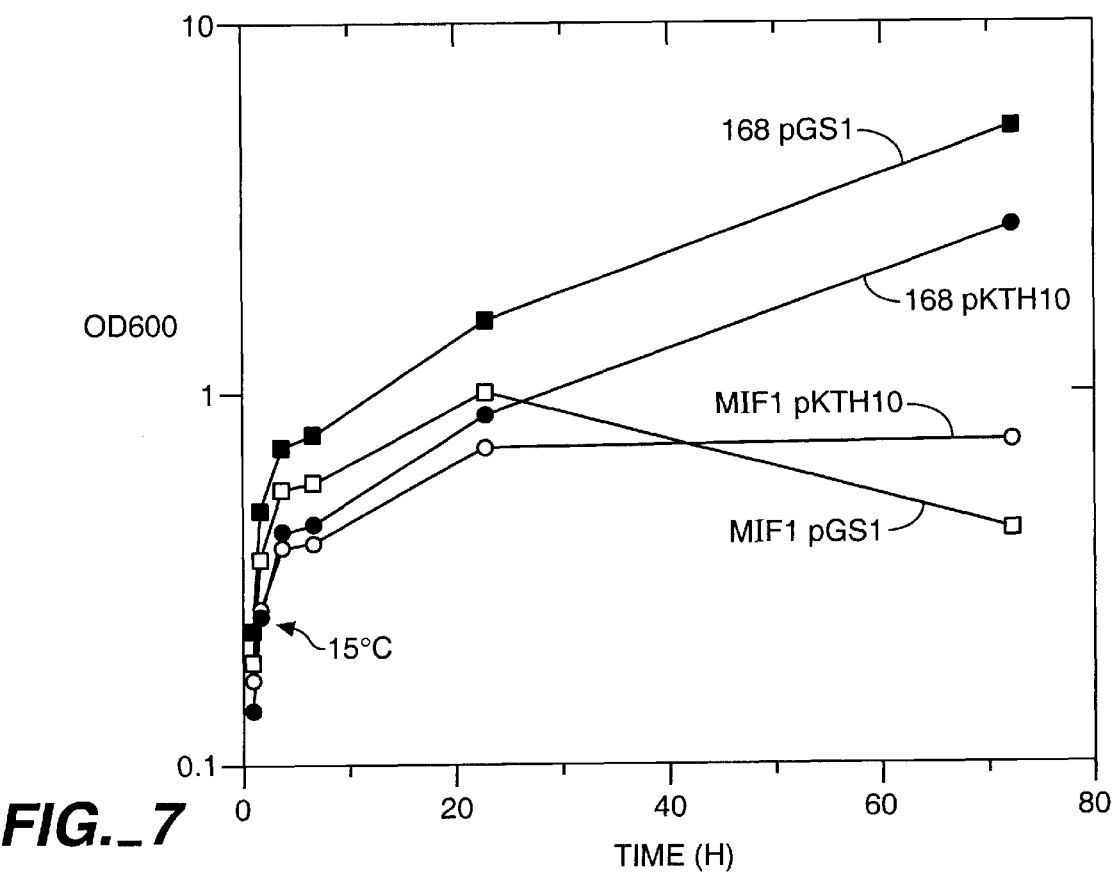
FIG._7

FIG._6A B. subtilis
queA → tgt → yrbF → yrzE → yrbG → spoVB → yrzD → secDF →

FIG._6B E. coli
queA → tgt → yajC → secD → secF →

```
          I
SECDF-BSU  M-KKGRLIAFFLFVLLIGTGLGYFTKPA--------------------------------                           27
SECD-ECO   MLNRYPLWKYVMLIVIVIGLLYALPNLFGEDPAVQITGARGVAASEQTLIQVQKTLQEEKITAKSVALEEGAILARSDS          80
           *  :  :   .: :  :.* * *

SECDF-BSU  ------------------ANNITLGLDLQGGFEVLYDVQPVKKGDKITKDVLVS-------                             63
SECD-ECO   TDTQLRAREALMGVMGDKYVVALNLAPATPRWLAAIHAEPMKLGLDLRGGVHFLMEVDMDTALGKLQEQNIDSLASDLRE         160
                             *****  **:  :       **** :** :* *          .  *
                                        D1

SECDF-BSU  ---------------------------------------------TVEALNRRANV                                  74
SECD-ECO   KGIPYTTVRKENNYGLSITFRDAKARDEAIAYLSKRHPDLVISSQGSNQLRAVMSDARLSEAREYAVQQNNILRNRVNQ         240
                                                          . *  *   * *

D2
SECDF-BSU  LGVSEPNIQIEGNNRIRVQLAGVTNQNRAREILATEAQLSFRDAND-------------------KELL                    124
SECD-ECO   LGVAEPVVQRQGADRIVVELPGIQDTARAKEILGATATLEFRLVNTNVDQAAAASGRVPGDSEVKQTREGQPVVLYKRVI         320
           ***:**:  .*.:***: : ** :: ***:*.*:  *  : :                       :

SECDF-BSU  NGADLVENGAKQTYDSTTNEPIVTIKLKDADKFGEVTKKVMKAPNNQLVIWLDYDKGDSFKKEVQKEHPKFVSAPNVSQ         204
SECD-ECO   LTGDHITDSTSSQDEYNQPQVNISLDSAGGNIMSNFTKDNIGKPMATLFVEYKDSGKKDANGRAVLVKQEEVINIANIQS         400
            ..* : : .::    : . : . :     :   * *  :  ** *: :::: *..*  :.  *::.    : *: *
```

FIG._6C-1

```
SECDF-BSU  ELNTTDVKIEGHFTAQEAKDLASILNAGALPVKLTEKYSTSVGAQFGQQALHDTVFAGIVGIAIIFLFMLFYYRLPGLIA  284
SECD-ECO   RLGNS-FRITGINNPNEARQLSLLIRAGALIAPIQIVEERTIGPTLGMQNIEQGLEACLAGLLVSILFMIIFYKKFGLIA  479
                .  .     .  *    ***      .       *   **  .      .  ****  .    ******
                                                      D3                    II       D4

SECDF-BSU  VITISVYIYITLQIFDW-MNAVLTLPGIAALILGVMAVDANITTYERIKEELKLGKSVRSAFRSGNRRSFATIFDANIT  363
SECD-ECO   TSALIANLILIVGIMSLLPGATLSMPGIAGIVLTLAVAVDANVLINERIKEELSNGRTVQQAIDEGYRGAFSSIFDANIT  524
                .                *            .        **** .  *******    .  .   ..*******
                    III                       IV                                D5

SECDF-BSU  TIIAAVVLFIFGTSSVKGFATMLILSILTSFITAVFLSRFLLALLVESRWLDRKKGWFGVNKKHIMDIQDTDENTEPHTP  443
SECD-ECO   TLIKVILLYAVGTGAIKGFAITGIGVATSMFTAIVGTRAIVNLLYGGKRVKKLSI                           615
                  *    **      ***.     . .    ..  *   .   .    **
                     V    D6                     VI

SECDF-BSU  --------FQKWDFTSKRKYFFIFSSAVTVAGIIILLVERLNLGIDFASGARIEVQSDHKLTTEQVEKDFESLGM      510
SECD-ECO   MAQEYTVEQLNHGRKVYDFMRWDYWAFGISGLLLIAAIVIMGVRGFNWGLDFTGGTVIEITLEKPAEIDVMRDALQKAGF  80
                    .  *      .  *  **  *  ..  . .  .       ***         .       ..
                                                              F1                VIII

SECDF-BSU  DPDTVVLSGEKSNIGVARFVGVPDKET------IAKVKTYFKDKYGSDPNVSTVSPTVGKELARNALYAVAIASIGIIIY  584
SECF-ECO   EEPMLQNFGSSHDIMVRMPPAEGETGGQVLGSQVLKVINESTNQNAAVKRIEFVGPSVGADLAQTGAMALMAALLSILVY  160
                       .    ** ..*  * ..        *    ..        ..  *   .     *    .. .* *
                                                                        X

SECDF-BSU  VSIRFEYKMAIAAIASLLYDAFFIVTFFSITRLEVDVTFIAAILTIIGYSINDTIVTFDRVREHMKKRKPKTFADLNHIV  664
SECF-ECO   VGFRFEWRLAAGVVIALAHDVIITLGIILSLFHIEIDLTIVASLMSVIGYSLNDSIVVSDRIRENFRKIRR---GTPYEIF  237
                  * .   .       *.  . ..      .. .    . * .*****.**.**    ** *. *  *
                                            F3                   F2
                                   IX               XI                       F4

SECDF-BSU  NLSLQQTFTTRSINTVLTVVLVVVTLLIFGASSITNFSIALLVGLLTGVYSSLXIAAQIWLAWKGR------ELKKDSAQ  737
SECF-ECO   NVSLTQTLHRTLITSGTTLMVILMLYLFGGPVLEGFSLTMLIGVSIGTASSIYVASALALKLGMKREHMLQQKVEKEGAD  317
                  *   * .          .   ***         .  .     .   **.        *
                                                                XII

SECF-ECO   QPSILP                                                                              323
```

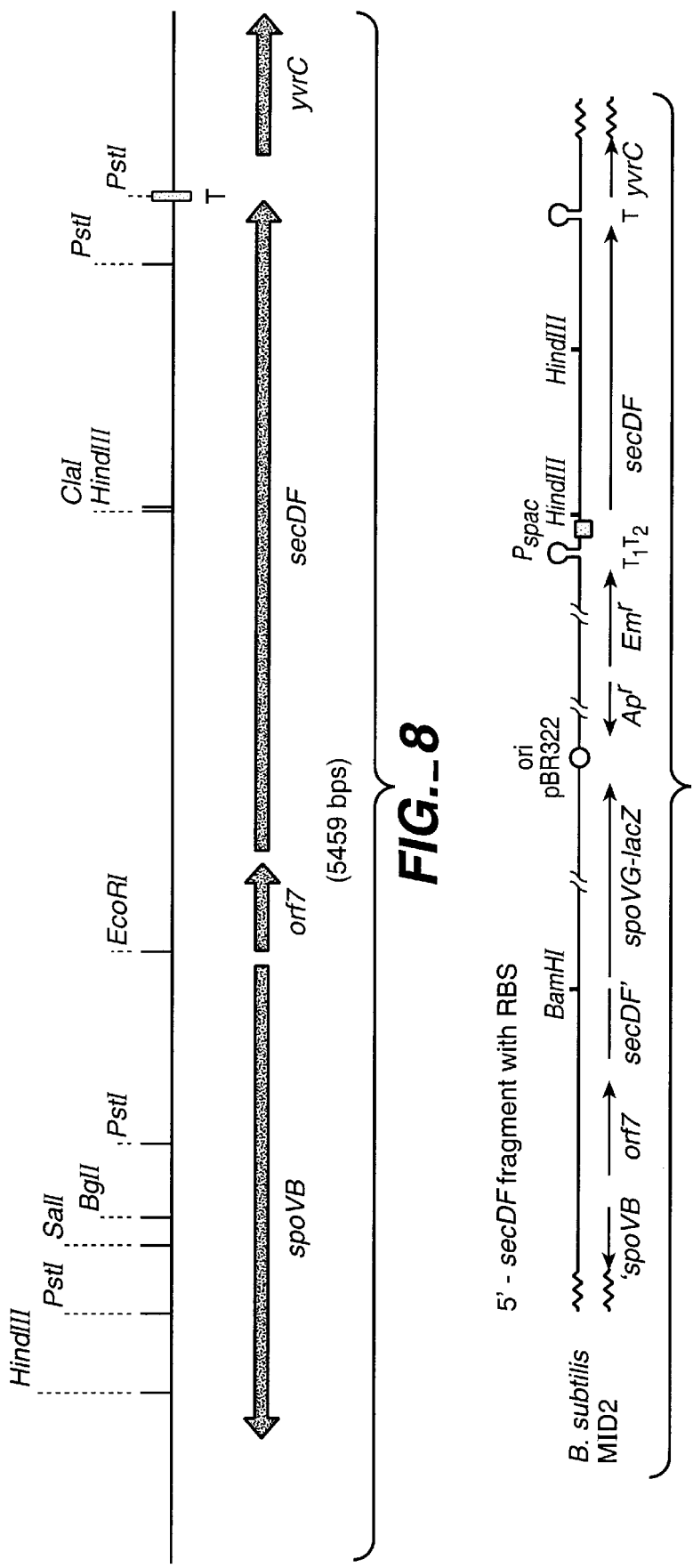
FIG._8
FIG._9A
FIG._9B

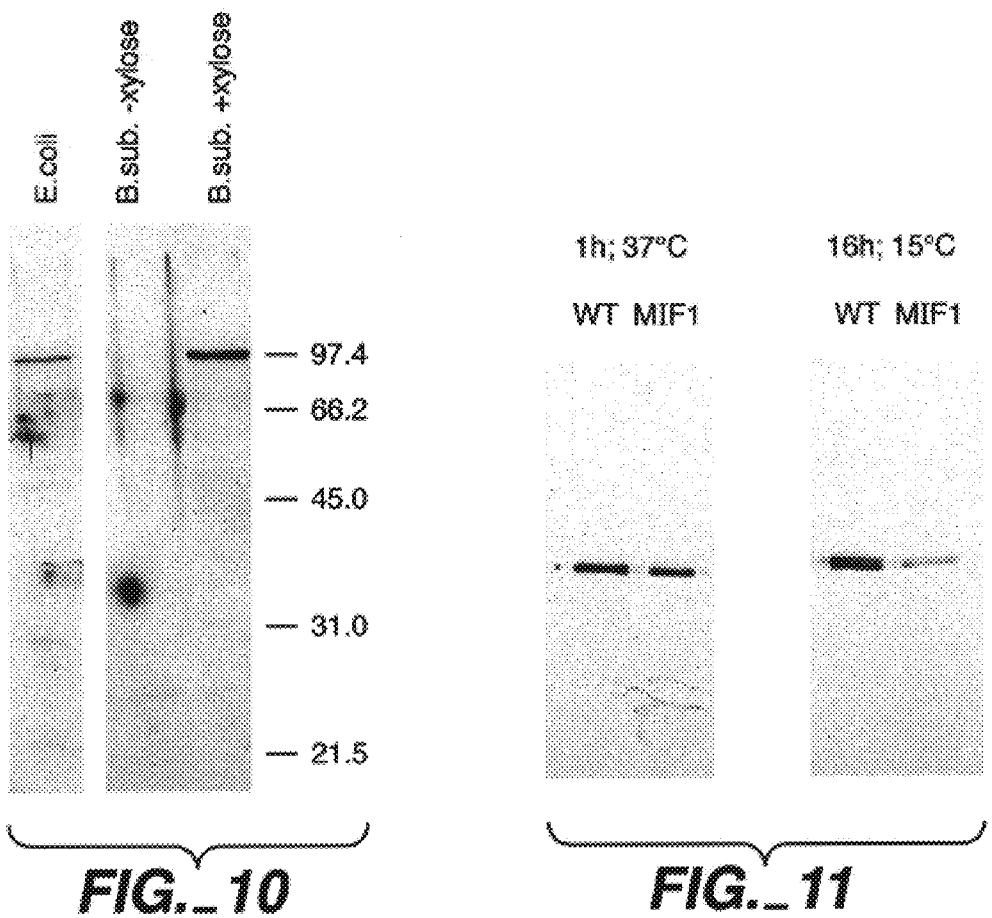
FIG._10
FIG._11
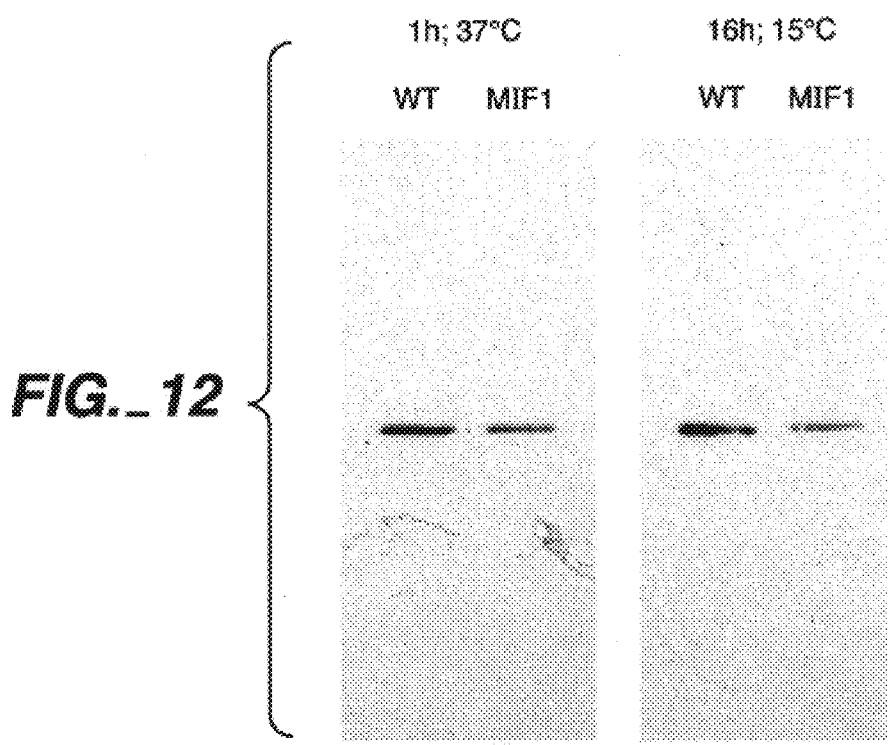
FIG._12

```
secdfnew.pep            LDLQGGFEVLYDVQPVKKGDKITKDVLVSTVEALNRRANVLGVSEPNIQIEGNNRIRVQL
                        40         50         60         70         80         90
                        ::   |     :|    |||||    :|    |:     |    :|:    ||    |:|
secd_ecoli              VISSQGSNQLRAVMSDARLSEAREYAVQQNINILRNRVNQLGVAEPVVQRQGADRIVVEL
                        210        220        230        240        250        260 secdfnew.pep            AGVTNQNRAREILATEAQLSFR--------------------DANDKELLNGADLVE----
                        100        110                                120        130
                        |::    ||::|  ||| | ||                     |::  |:   :|
secd_ecoli              PGIQDTARAKEILGATATLEFRLVNTNVDQAAAASGRVPGDSEVKQTREGQPVVLYKRVI
                        270        280        290        300        310        320 secdfnew.pep            -NGAKQTYDSTT-----NEPIVTIKLKDA--DKFGEVTKKVMKMAPNNQLVIWLDYDKGD
                                140             150             160        170        180
                        :|| |:  |::      |:|  | ||:|   ||:|  |    :|  :    |:|  ||
secd_ecoli              LTGDHIT-DSTSSQDEYNQPQVNISLDSAGGNIMSNFTKDNIGKPMATLFVEYKDSGKKD
                                330        340        350        360        370 secdfnew.pep            SFKKEVQKEHPKFVSAPNVSQELNTTDVKIEGHFTAQEAKDLASILNAGAL--PVKLTEK
                        190        200        210        220        230        240
                        ::     :   :      ::     :|  |       ::|:|  :| ||||    ::|:
secd_ecoli              ANGRAVLVKQEEVINIANIQSRLGNS-FRITGINNPNEARQLSLLLRAGALIAPIQIVEE
                        380        390        400        410        420        430 secdfnew.pep            YSTSVGAQFGQQALHDTVFAGIVGIAIIFLFMLFYYRLPGLIAVITLSVIYITLQIFDW
                        250        260        270        280        290        300
                        ::  ::  :   |    ::: ::  | ||| :::|||||:||:::  :|:  |::|:|
secd_ecoli              RT--IGPTLGMQNIEQGLEACLAGLLVSILFMIIFYKKFGLIATSALIANLILIVGIMSL
                        440        450        460        470        480        490
```

FIG._13

```
secdfbsupep   250        260        270        280        290        300
              LDRKKGWFGVNKKHIMDIQDTDENTEPHTPFQKWDFTSKRKYFFIFSSAVTVAGIIILLV
                                                  :::|::  : |::|:: |   |::|::|:
SECF_ECOLI                            MAQEYTVEQLNHGRKVYDFMRWDY----WAFGISGLLLIAAIVIMGV
                                      10         20         30         40 secdfbsupep   310        320        330        340        350        360
              FRLNLGIDFASGARIEVQSDHKLTTEQVEKDFESLGMDPDTVVLSGEKSNIGVARFVGVP
              |:  |||::|| |||| :||   || |||  :|| ||                 | :|
SECF_ECOLI    RGFNWGLDFTGGTVIEITLEKPAEIDVMRDALQKAGFEEPMLQNFGSSHDI----MVRMP
              50         60         70         80         90 secdfbsupep   370        380        390        400        410
              DKE-------TIAKVKTYFKDKYGSDPNVSTVSPTVGKELARNALYAVAIASIGIII
                :                   :  :  ::|:::|:|  :::|::  |::|:|:
SECF_ECOLI    PAEGETGGQVLGSQVLKVINESTNQNAAVKRIEFVGPSVGADLAQTGAMALMAALLSILV
              100        110        120        130        140        150 secdfbsupep   420        430        440        450        460        470
              YVSIRFEYKMAIAAIASLLYDAFFIVTFFSITRLEVDVTFIAAILTIIGYSINDTIVTFD
              |::|||  |  : |||   ||:|::|:|: :|||| :||||:| :|:|||::|:::|:
SECF_ECOLI    YVGFRFEWRLAAGVVIALAHDVIITLGILSLFHIEIDLTIVASLMSVIGYSLNDSIVVSD
              160        170        180        190        200        210 secdfbsupep   480        490        500        510        520        530
              RVREHMKK-RKPKTFADLNHIVNLSLQQTFTRSINTVLTVVIVVVTLLIFGASSITNFSI
              ||||: ::   |::  : |    ::       :|::|:|:: ::::|:|||:|::|:|:
SECF_ECOLI    RIRENFRKIRRGTPY---EIFNVSLTQTLHRTLITSGTTLMVILMLYLFGGPVLEGFSL
              220        230        240        250        260        270 secdfbsupep   540        550        560        570
              ALLVGLLTGVYSSLYIAAQIWLAWKGRELKKKDSAQ
              :::|::  ||::|:|    ::|::::::
SECF_ECOLI    TMLIGVSIGTASSIYVASALALKLGMKREHMLQQKVEKEGADQPSILP
              280        290        300        310        320
```

FIG._14

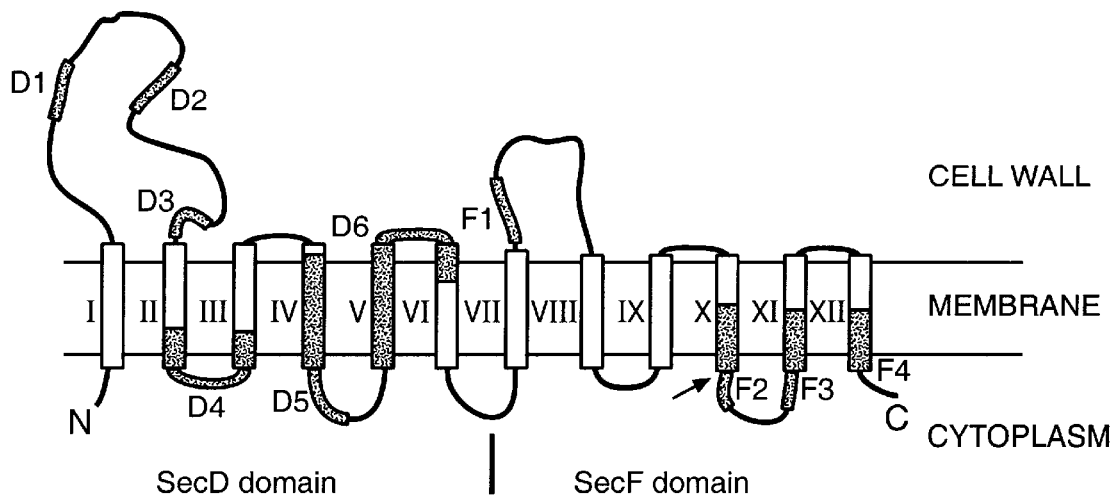
FIG._15
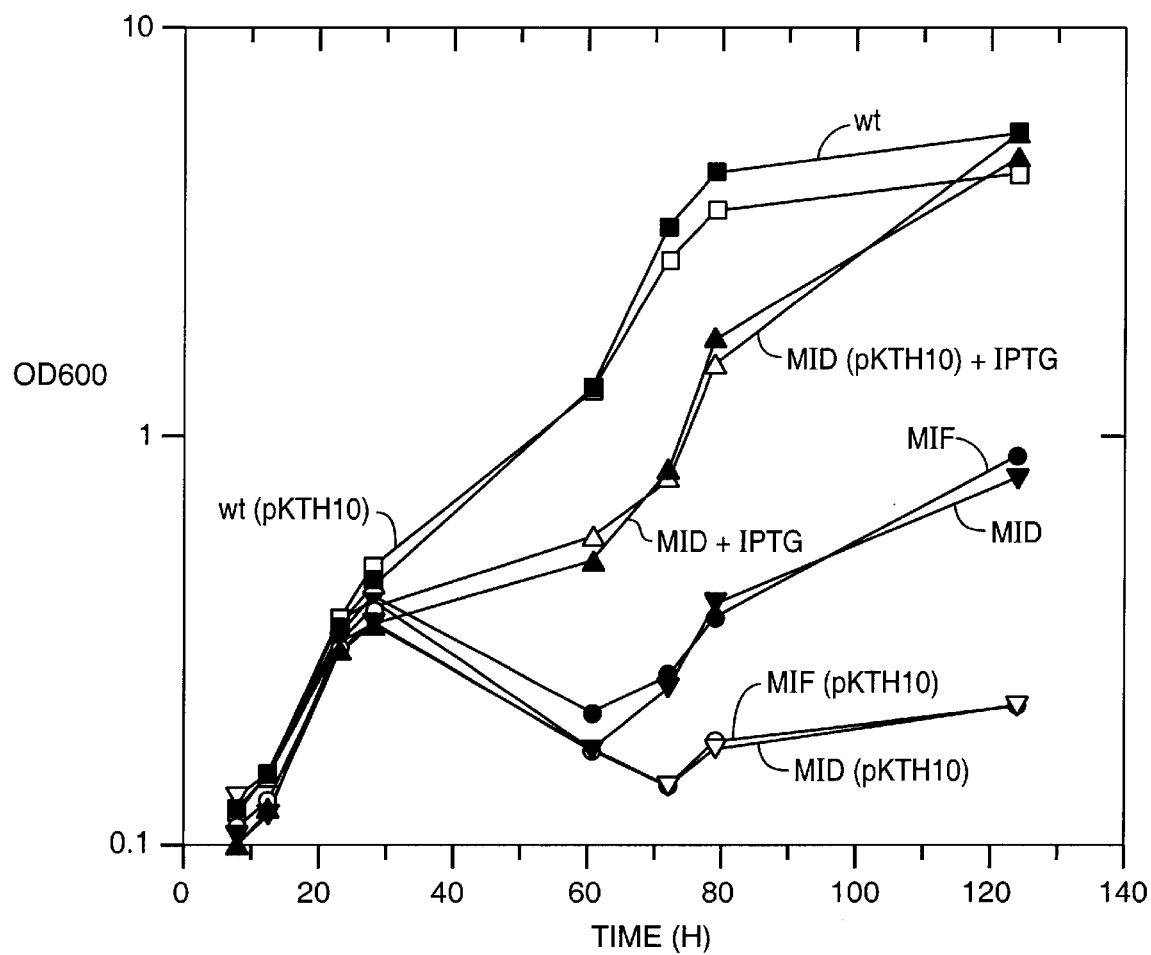
FIG._16C

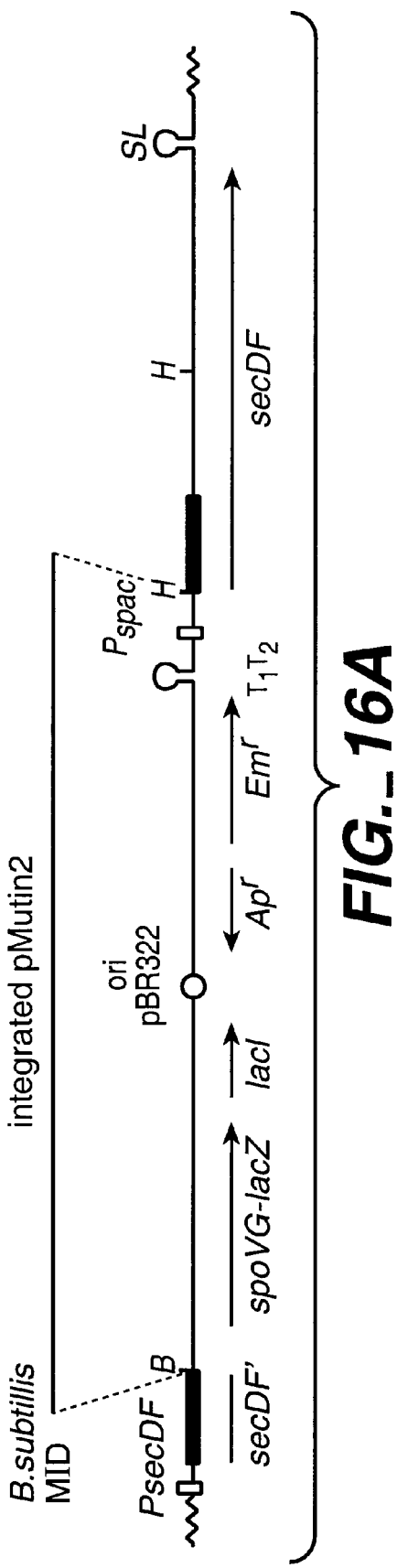
FIG._16A
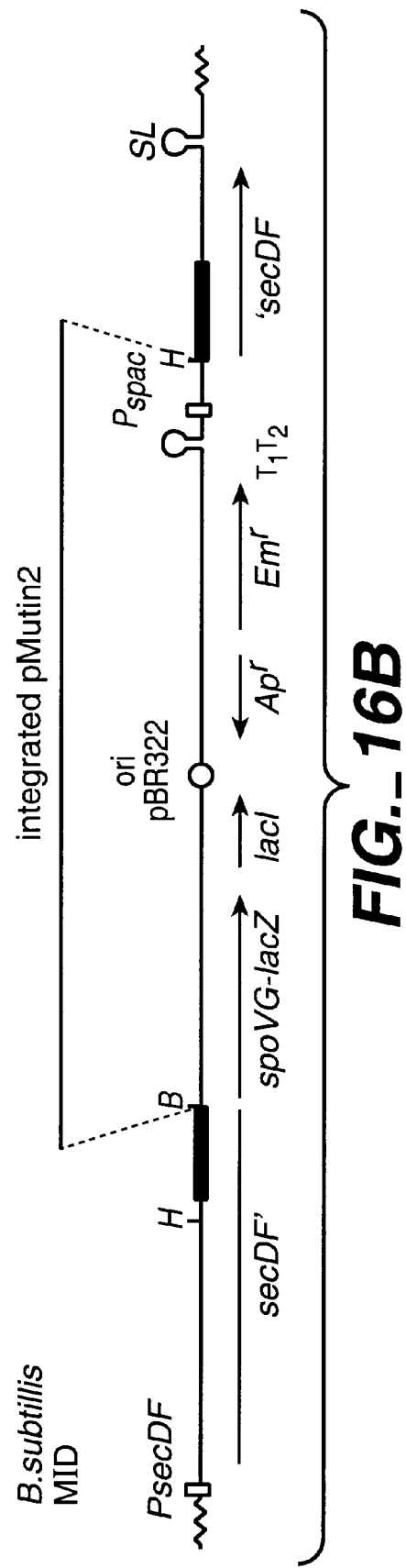
FIG._16B

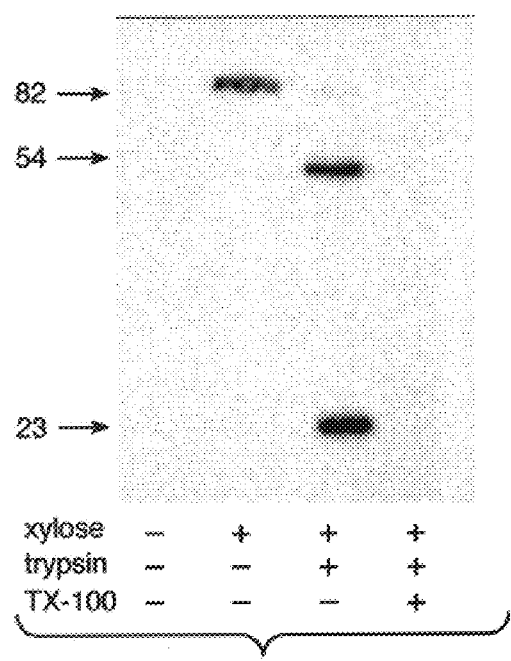
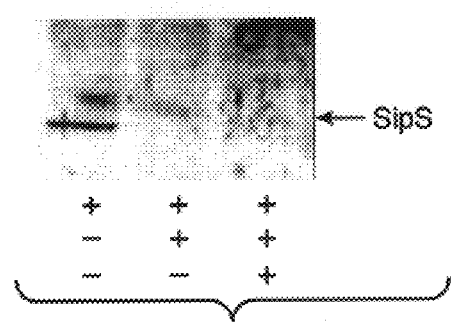
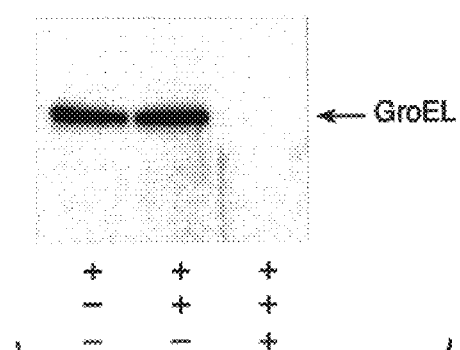
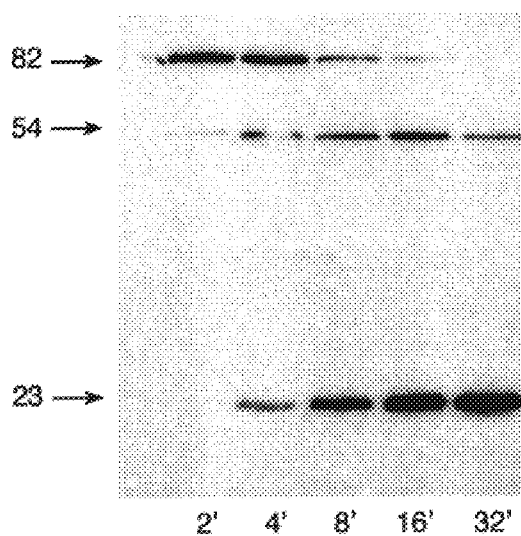
FIG._17A
FIG._17B
FIG._17C
FIG._17D

SEQUENCE LISTING

<160> NUMBER OF SEQ ID NOS: 4

<210> SEQ ID NO 1
<211> LENGTH: 2211
<212> TYPE: DNA
<213> ORGANISM: Bacillus Subtilis

<400> SEQUENCE: 1

```
atgaaaaaag gacgcttgat tgcgtttttc cttttcgttc tattgatcgg cacgggcttg      60
ggctacttta cgaagcctgc cgctaacaat attacgttag gattggattt gcaaggcgga     120
tttgaggtgc tgtatgatgt acagcctgta aaaaaggtg acaaaatcac aaaagacgtt     180
ctggtcagca cagtagaggc actgaaccgc cgggccaatg ttctcggtgt cagcgaaccg     240
aacatccaaa ttgaagggaa taccggatt cgcgttcagc tcgctggcgt gacaaaccaa     300
aacagagcgc gtgaaatttt ggcgactgaa gcgcagcttt ctttcagaga tgcaaacgat     360
aaggaactgt taaacggtgc tgatctagtc gaaaacggcg ctaaacaaac ttatgatagc     420
acaacaaatg agccaattgt cacgattaag ctgaaagacg ctgataaatt tggtgaagtg     480
accaagaagg tcatgaaaat ggcgccaaac aaccagcttg tcatttggtt ggattatgat     540
aaaggtgatt cctttaagaa agaagttcaa aaagagcatc ctaaatttgt atccgctcca     600
aatgtaagtc aggaactaaa tacaactgat gtaaaaattg aaggtcattt cacagctcaa     660
gaagcgaaag atttagccag cattttaaac gcaggcgcac ttcctgtgaa actgactgaa     720
aagtattcga catcagtagg cgcgcaattc ggccagcagg ctctccatga tacggtgttt     780
gccggtattg tcggtatcgc aattattttc ttatttatgc ttttctatta ccgtctgccg     840
ggattaatcg cggtgattac gctgtctgtt tatatctaca ttacactcca gatctttgac     900
tggatgaatg ccgtactcac gcttccggga attgccgctc tcatttagg tgtcgggatg     960 gctgttgacg ccaacattat tacctatgag cggattaaag aagagctcaa gctaggaaag    1020
tcagtccgct ctgccttccg ttcaggaaac agacggtcat ttgcgacgat ttttgacgcg    1080
aatattacaa ccattattgc agcggttgtg ctctttatct ttgggacaag ctctgttaaa    1140
gggtttgcga caatgctgat cctatcgatt ttgacaagct ttatcactgc cgttttctta    1200
tcgagatttc tcctcgctct ccttgtggaa agcagatggc ttgatcggaa aaaaggctgg    1260
tttggtgtca ataagaaaca tatcatggat attcaggata cggatgaaaa tacagagccg    1320
```

```
catacgccat tccaaaaatg ggatttcacg agcaaacgca aatacttctt tattttctcc   1380
agtgcggtca cggttgccgg gattattatc ctgcttgtgt tcaggctgaa tcttggcatt   1440
gactttgcaa gcggtgcacg gattgaagtg caaagcgacc ataagctgac gacagagcaa   1500
gttgagaagg atttttgaatc tctgggtatg gaccctgata ctgtagttct gtcaggcgaa   1560
aagagcaata tcggtgttgc ccgttttgtc ggggtgccag ataaagaaac cattgcaaaa   1620
gtaaaaacgt attttaaaga caaatacgga tctgatccaa atgtcagcac agtttcaccg   1680
acagtcggta aggagctggc gagaaatgcg ctgtacgcag ttgctatagc ttctattggc   1740
atcattattt acgtttcaat ccgattcgaa tacaaaatgg cgattgctgc catcgcctca   1800
ttgctatatg acgcattctt tatcgtcacg ttcttcagta ttacaaggct tgaggtagat   1860
gttacattca tcgcggccat cttgacgata atcgggtatt ccattaacga tacaatcgtt   1920
acatttgaca gggtccgcga gcatatgaaa aagcgtaagc cgaaaacctt tgccgatctg   1980
aaccatattg taaacctgag cctgcagcaa acctttacac gttcaattaa cactgtatta   2040
accgttgtga ttgttgttgt gacattgctg atctttggag catcttctat tactaacttc   2100
tcaattgctt tattggtcgg gctgttaaca ggcgtttatt cttctctata cattgccgca   2160
caaatttggc ttgcatggaa aggaagagaa ctgaaaaaag attcggcgca a             2211
```

<210> SEQ ID NO 2
<211> LENGTH: 737
<212> TYPE: PRT
<213> ORGANISM: Bacillus Subtilis

<400> SEQUENCE: 2

```
Met Lys Lys Gly Arg Leu Ile Ala Phe Phe Leu Phe Val Leu Leu Ile
  1               5                  10                  15

Gly Thr Gly Leu Gly Tyr Phe Thr Lys Pro Ala Ala Asn Asn Ile Thr
             20                  25                  30

Leu Gly Leu Asp Leu Gln Gly Gly Phe Glu Val Leu Tyr Asp Val Gln
         35                  40                  45

Pro Val Lys Lys Gly Asp Lys Ile Thr Lys Asp Val Leu Val Ser Thr
     50                  55                  60

Val Glu Ala Leu Asn Arg Arg Ala Asn Val Leu Gly Val Ser Glu Pro
 65                  70                  75                  80

Asn Ile Gln Ile Glu Gly Asn Asn Arg Ile Arg Val Gln Leu Ala Gly
                 85                  90                  95

Val Thr Asn Gln Asn Arg Ala Arg Glu Ile Leu Ala Thr Glu Ala Gln
            100                 105                 110

Leu Ser Phe Arg Asp Ala Asn Asp Lys Glu Leu Leu Asn Gly Ala Asp
        115                 120                 125

Leu Val Glu Asn Gly Ala Lys Gln Thr Tyr Asp Ser Thr Thr Asn Glu
    130                 135                 140

Pro Ile Val Thr Ile Lys Leu Lys Asp Ala Asp Lys Phe Gly Glu Val
145                 150                 155                 160

Thr Lys Lys Val Met Lys Met Ala Pro Asn Asn Gln Leu Val Ile Trp
                165                 170                 175

Leu Asp Tyr Asp Lys Gly Asp Ser Phe Lys Lys Glu Val Gln Lys Glu
            180                 185                 190

His Pro Lys Phe Val Ser Ala Pro Asn Val Ser Gln Glu Leu Asn Thr
        195                 200                 205

Thr Asp Val Lys Ile Glu Gly His Phe Thr Ala Gln Glu Ala Lys Asp
```

-continued

```
               210                 215                 220
Leu Ala Ser Ile Leu Asn Ala Gly Ala Leu Pro Val Lys Leu Thr Glu
225                 230                 235                 240

Lys Tyr Ser Thr Ser Val Gly Ala Gln Phe Gly Gln Gln Ala Leu His
                245                 250                 255

Asp Thr Val Phe Ala Gly Ile Val Gly Ile Ala Ile Ile Phe Leu Phe
                260                 265                 270

Met Leu Phe Tyr Tyr Arg Leu Pro Gly Leu Ile Ala Val Ile Thr Leu
                275                 280                 285

Ser Val Tyr Ile Tyr Ile Thr Leu Gln Ile Phe Asp Trp Met Asn Ala
                290                 295                 300

Val Leu Thr Leu Pro Gly Ile Ala Ala Leu Ile Leu Gly Val Gly Met
305                 310                 315                 320

Ala Val Asp Ala Asn Ile Ile Thr Tyr Glu Arg Ile Lys Glu Glu Leu
                325                 330                 335

Lys Leu Gly Lys Ser Val Arg Ser Ala Phe Arg Ser Gly Asn Arg Arg
                340                 345                 350

Ser Phe Ala Thr Ile Phe Asp Ala Asn Ile Thr Thr Ile Ile Ala Ala
                355                 360                 365

Val Val Leu Phe Ile Phe Gly Thr Ser Ser Val Lys Gly Phe Ala Thr
                370                 375                 380

Met Leu Ile Leu Ser Ile Leu Thr Ser Phe Ile Thr Ala Val Phe Leu
385                 390                 395                 400

Ser Arg Phe Leu Leu Ala Leu Leu Val Glu Ser Arg Trp Leu Asp Arg
                405                 410                 415

Lys Lys Gly Trp Phe Gly Val Asn Lys Lys His Ile Met Asp Ile Gln
                420                 425                 430

Asp Thr Asp Glu Asn Thr Glu Pro His Thr Pro Phe Gln Lys Trp Asp
                435                 440                 445

Phe Thr Ser Lys Arg Lys Tyr Phe Phe Ile Phe Ser Ser Ala Val Thr
                450                 455                 460

Val Ala Gly Ile Ile Ile Leu Leu Val Phe Arg Leu Asn Leu Gly Ile
465                 470                 475                 480

Asp Phe Ala Ser Gly Ala Arg Ile Glu Val Gln Ser Asp His Lys Leu
                485                 490                 495

Thr Thr Glu Gln Val Glu Lys Asp Phe Glu Ser Leu Gly Met Asp Pro
                500                 505                 510

Asp Thr Val Val Leu Ser Gly Glu Lys Ser Asn Ile Gly Val Ala Arg
                515                 520                 525

Phe Val Gly Val Pro Asp Lys Glu Thr Ile Ala Lys Val Lys Thr Tyr
                530                 535                 540

Phe Lys Asp Lys Tyr Gly Ser Asp Pro Asn Val Ser Thr Val Ser Pro
545                 550                 555                 560

Thr Val Gly Lys Glu Leu Ala Arg Asn Ala Leu Tyr Ala Val Ala Ile
                565                 570                 575

Ala Ser Ile Gly Ile Ile Ile Tyr Val Ser Ile Arg Phe Glu Tyr Lys
                580                 585                 590

Met Ala Ile Ala Ala Ile Ala Ser Leu Leu Tyr Asp Ala Phe Phe Ile
                595                 600                 605

Val Thr Phe Phe Ser Ile Thr Arg Leu Glu Val Asp Val Thr Phe Ile
                610                 615                 620

Ala Ala Ile Leu Thr Ile Ile Gly Tyr Ser Ile Asn Asp Thr Ile Val
625                 630                 635                 640
```

```
Thr Phe Asp Arg Val Arg Glu His Met Lys Lys Arg Pro Lys Thr
                    645                 650                 655

Phe Ala Asp Leu Asn His Ile Val Asn Leu Ser Leu Gln Gln Thr Phe
                660                 665                 670

Thr Arg Ser Ile Asn Thr Val Leu Thr Val Ile Val Val Thr
            675                 680                 685

Leu Leu Ile Phe Gly Ala Ser Ser Ile Thr Asn Phe Ser Ile Ala Leu
            690                 695                 700

Leu Val Gly Leu Leu Thr Gly Val Tyr Ser Ser Leu Tyr Ile Ala Ala
705                 710                 715                 720

Gln Ile Trp Leu Ala Trp Lys Gly Arg Glu Leu Lys Lys Asp Ser Ala
                725                 730                 735

Gln
```

```
<210> SEQ ID NO 3
<211> LENGTH: 615
<212> TYPE: PRT
<213> ORGANISM: E. coli

<400> SEQUENCE: 3
```

```
Met Leu Asn Arg Tyr Pro Leu Trp Lys Tyr Val Met Leu Ile Val Val
1               5                   10                  15

Ile Val Ile Gly Leu Leu Tyr Ala Leu Pro Asn Leu Phe Gly Glu Asp
                20                  25                  30

Pro Ala Val Gln Ile Thr Gly Ala Arg Gly Val Ala Ala Ser Glu Gln
            35                  40                  45

Thr Leu Ile Gln Val Gln Lys Thr Leu Gln Glu Glu Lys Ile Thr Ala
        50                  55                  60

Lys Ser Val Ala Leu Glu Glu Gly Ala Ile Leu Ala Arg Phe Asp Ser
65              70                  75                  80

Thr Asp Thr Gln Leu Arg Ala Arg Glu Ala Leu Met Gly Val Met Gly
                85                  90                  95

Asp Lys Tyr Val Val Ala Leu Asn Leu Ala Pro Ala Thr Pro Arg Trp
            100                 105                 110

Leu Ala Ala Ile His Ala Glu Pro Met Lys Leu Gly Leu Asp Leu Arg
        115                 120                 125

Gly Gly Val His Phe Leu Met Glu Val Asp Met Asp Thr Ala Leu Gly
    130                 135                 140

Lys Leu Gln Glu Gln Asn Ile Asp Ser Leu Arg Ser Asp Leu Arg Glu
145                 150                 155                 160

Lys Gly Ile Pro Tyr Thr Thr Val Arg Lys Glu Asn Asn Tyr Gly Leu
                165                 170                 175

Ser Ile Thr Phe Arg Asp Ala Lys Ala Arg Asp Glu Ala Ile Ala Tyr
            180                 185                 190

Leu Ser Lys Arg His Pro Asp Leu Val Ile Ser Ser Gln Gly Ser Asn
        195                 200                 205

Gln Leu Arg Ala Val Met Ser Asp Ala Arg Leu Ser Glu Ala Arg Glu
    210                 215                 220

Tyr Ala Val Gln Gln Asn Ile Asn Ile Leu Arg Asn Arg Val Asn Gln
225                 230                 235                 240

Leu Gly Val Ala Glu Pro Val Val Gln Arg Gln Gly Ala Asp Arg Ile
                245                 250                 255

Val Val Glu Leu Pro Gly Ile Gln Asp Thr Ala Arg Ala Lys Glu Ile
            260                 265                 270
```

```
Leu Gly Ala Thr Ala Thr Leu Glu Phe Arg Leu Val Asn Thr Asn Val
            275                 280                 285

Asp Gln Ala Ala Ala Ser Gly Arg Val Pro Gly Asp Ser Glu Val
    290                 295                 300

Lys Gln Thr Arg Glu Gly Gln Pro Val Val Leu Tyr Lys Arg Val Ile
305                 310                 315                 320

Leu Thr Gly Asp His Ile Thr Asp Ser Thr Ser Ser Gln Asp Glu Tyr
                325                 330                 335

Asn Gln Pro Gln Val Asn Ile Ser Leu Asp Ser Ala Gly Gly Asn Ile
            340                 345                 350

Met Ser Asn Phe Thr Lys Asp Asn Ile Gly Lys Pro Met Ala Thr Leu
            355                 360                 365

Phe Val Glu Tyr Lys Asp Ser Gly Lys Lys Asp Ala Asn Gly Arg Ala
            370                 375                 380

Val Leu Val Lys Gln Glu Glu Val Ile Asn Ala Asn Ile Gln Ser
385                 390                 395                 400

Arg Leu Gly Asn Ser Phe Arg Ile Thr Gly Ile Asn Asn Pro Asn Glu
                405                 410                 415

Ala Arg Gln Leu Ser Leu Leu Arg Ala Gly Ala Leu Ile Ala Pro
            420                 425                 430

Ile Gln Ile Val Glu Glu Arg Thr Ile Gly Pro Thr Leu Gly Met Gln
            435                 440                 445

Asn Ile Glu Gln Gly Leu Glu Ala Cys Leu Ala Gly Leu Leu Val Ser
    450                 455                 460

Ile Leu Phe Met Ile Ile Phe Tyr Lys Lys Phe Gly Leu Ile Ala Thr
465                 470                 475                 480

Ser Ala Leu Ile Ala Asn Leu Ile Leu Ile Val Gly Ile Met Ser Leu
                485                 490                 495

Leu Pro Gly Ala Thr Leu Ser Met Pro Gly Ile Ala Gly Ile Val Leu
            500                 505                 510

Thr Leu Ala Val Ala Val Asp Ala Asn Val Leu Ile Asn Glu Arg Ile
            515                 520                 525

Lys Glu Glu Leu Ser Asn Gly Arg Thr Val Gln Gln Ala Ile Asp Glu
530                 535                 540

Gly Tyr Arg Gly Ala Phe Ser Ser Ile Phe Asp Ala Asn Ile Thr Thr
545                 550                 555                 560

Leu Ile Lys Val Ile Leu Tyr Ala Val Gly Thr Gly Ala Ile Lys
                565                 570                 575

Gly Phe Ala Ile Thr Thr Gly Ile Gly Val Ala Thr Ser Met Phe Thr
            580                 585                 590

Ala Ile Val Gly Thr Arg Ala Ile Val Asn Leu Leu Tyr Gly Gly Lys
            595                 600                 605

Arg Val Lys Lys Leu Ser Ile
    610                 615

<210> SEQ ID NO 4
<211> LENGTH: 323
<212> TYPE: PRT
<213> ORGANISM: E. coli

<400> SEQUENCE: 4

Met Ala Gln Glu Tyr Thr Val Glu Gln Leu Asn His Gly Arg Lys Val
1               5                   10                  15

Tyr Asp Phe Met Arg Trp Asp Tyr Trp Ala Phe Gly Ile Ser Gly Leu
```

-continued

```
            20                  25                  30
Leu Leu Ile Ala Ala Ile Val Ile Met Gly Val Arg Gly Phe Asn Trp
        35                  40                  45

Gly Leu Asp Phe Thr Gly Gly Thr Val Ile Glu Ile Thr Leu Glu Lys
    50                  55                  60

Pro Ala Glu Ile Asp Val Met Arg Asp Ala Leu Gln Lys Ala Gly Phe
65                  70                  75                  80

Glu Glu Pro Met Leu Gln Asn Phe Gly Ser Ser His Asp Ile Met Val
                85                  90                  95

Arg Met Pro Pro Ala Glu Gly Glu Thr Gly Gly Gln Val Leu Gly Ser
            100                 105                 110

Gln Val Leu Lys Val Ile Asn Glu Ser Thr Asn Gln Asn Ala Ala Val
        115                 120                 125

Lys Arg Ile Glu Phe Val Gly Pro Ser Val Gly Ala Asp Leu Ala Gln
    130                 135                 140

Thr Gly Ala Met Ala Leu Met Ala Ala Leu Leu Ser Ile Leu Val Tyr
145                 150                 155                 160

Val Gly Phe Arg Phe Glu Trp Arg Leu Ala Ala Gly Val Val Ile Ala
                165                 170                 175

Leu Ala His Asp Val Ile Ile Thr Leu Gly Ile Leu Ser Leu Phe His
            180                 185                 190

Ile Glu Ile Asp Leu Thr Ile Val Ala Ser Leu Met Ser Val Ile Gly
        195                 200                 205

Tyr Ser Leu Asn Asp Ser Ile Val Val Ser Asp Arg Ile Arg Glu Asn
    210                 215                 220

Phe Arg Lys Ile Arg Arg Gly Thr Pro Tyr Glu Ile Phe Asn Val Ser
225                 230                 235                 240

Leu Thr Gln Thr Leu His Arg Thr Leu Ile Thr Ser Gly Thr Thr Leu
                245                 250                 255

Met Val Ile Leu Met Leu Tyr Leu Phe Gly Gly Pro Val Leu Glu Gly
            260                 265                 270

Phe Ser Leu Thr Met Leu Ile Gly Val Ser Ile Gly Thr Ala Ser Ser
        275                 280                 285

Ile Tyr Val Ala Ser Ala Leu Ala Leu Lys Leu Gly Met Lys Arg Glu
    290                 295                 300

His Met Leu Gln Gln Lys Val Glu Lys Glu Gly Ala Asp Gln Pro Ser
305                 310                 315                 320

Ile Leu Pro
```

US 6,630,328 B2

INCREASING PRODUCTION OF PROTEINS IN GRAM-POSITIVE MICROORGANISMS

This is a continuation of application Ser. No. 09/462,844, now U.S. Pat. No. 6,258,563 filed Mar. 22, 2000, which is a 371 of PCT/US98/14786 file Jul. 15, 1998.

FIELD OF THE INVENTION

The present invention generally relates to expression of proteins in gram-positive microorganisms and specifically to the gram positive microorganism secretion factor SecDF. The present invention provides expression vectors, methods and systems for the production of proteins in gram-positive microorganisms.

BACKGROUND OF THE INVENTION

Gram-positive microorganisms, such as members of the group Bacillus, have been used for large-scale industrial fermentation due, in part, to their ability to secrete their fermentation products into the culture media. In gram-positive bacteria, secreted proteins are exported across a cell membrane and a cell wall, and then are subsequently release into the external media usually obtaining their native conformation.

Secretion factors from Gram-positive microorganisms which have been identified and reported in the literature include SecA (Sadaie Y., Takamatsu h., Nakamura k., Yamane k.; Gene 98:101–105, 1991)., SecY (Suh J.-W., Boylan S. A., Thomas S. M., Dolan K. M., Oliver D. B., Price C. W.; Mol. Microbiol. 4:305–314, 1990)., SecE (Jeong S., Yoshikawa H., Takahashi H.; Mol. Microbiol. 10:133–142, 1993), FtsY an FfH (PCT/NL 96/00278), and PrsA (WO 94/19471).

By contrast, in the gram-negative microorganism, E.coli, protein is transported to the periplasm rather than across the cell membrane and cell wall and into the culture media. E.coli has at least two types of components of the secretory mechanism, soluble cytoplasmic proteins and membrane associated proteins. Reported E.coli secretion factors include the soluble cytoplasmic proteins, SecB and heat shock proteins; the peripheral membrane-associated protein SecA; and the integral membrane proteins SecY, SecE, SecD and SecF.

In spite of advances in understanding portions of the protein secretion machinery in procaryotic cells, the complete mechanism of protein secretion, especially for gram-positive microorganisms, such as Bacillus, has yet to be fully elucidated.

SUMMARY OF THE INVENTION

The capacity of the secretion machinery of a Gram-positive microorganism may become a limiting factor or bottleneck to protein secretion and the production of proteins in secreted form, in particular when the proteins are recombinantly introduced and overexpressed by the host cell. The present invention provides a means for alleviating that bottle neck.

The present invention is based, in part, upon the identification of the Bacillus secretion factor SecDF and upon the unexpected finding that, in contrast to SecD and SecF of E.coli, Bacillus SecDF is encoded by one nucleic acid sequence. The present invention is also based upon the unexpected finding that SecDF has sequence as well as structural similarity to secondary solute transporters.

The present invention is also based, in part, upon the finding that SecDF mutants of B.subtilis have a cold-sensitive phenotype for growth and further that the rate of processing of exo-enzymes, amylase and neutral protease, is decreased in SecDF mutants of B.subtilis. The present invention is also based, in part, upon the finding that B.subtilis SecDF, which has twelve putative transmembrane domains is required for efficient translocation of secretory pre-proteins under conditions of hyper-secretion.

The present invention provides isolated nucleic acid and amino acid sequences for B. subtilla SecD, SecF and SecDF. The amino acid sequence and nucleic acid sequence for B. subtilis SecDF is shown in FIGS. 1A–1E, SEQ ID NO: 1 and SEQ ID NO: 2.

The present invention also provides improved methods for secreting proteins from gram-positive microorganisms. Accordingly, the present invention provides an improved method for secreting desired proteins in a gram-positive microorganism comprising the steps of obtaining a gram positive microorganism comprising nucleic acid encoding at least one Bacillus secretion factor selected from the group consisting of SecD, SecF and SecDF wherein said secretion factor is under the control of expression signals capable of expressing said secretion factor in a gram-positive microorganism said microorganism further comprising nucleic acid encoding said protein; and culturing said microorganism under conditions suitable for expression of said secretion factor and secretion of said protein. In one embodiment of the present invention, the protein is homologous or naturally occurring in the gram-positive microorganism. In another embodiment of the present invention, the protein is heterologous to the gram-positive microorganism.

The present invention provides expression vectors and host cells comprising at least one nucleic acid encoding a gram-positive secretion factor selected from the group consisting of SecD, SecF and SecDF. In one embodiment of the present invention, the host cell is genetically engineered to produce a desired protein, such as an enzyme, growth factor or hormone. In yet another embodiment of the present invention, the enzyme is selected from the group consisting of proteases, carbohydrases including amylases, cellulases, xylanases, reductases and lipases; isomerases such as racemases, epimerases, tautomerases, or mutases; transferases, kinases and phophatases acylases, amidases, esterases, oxidases.

In a further embodiment the expression of the secretion factor SecD, SecF and/or SecDF is coordinated with the expression of other components of the secretion machinery. Preferably other components of the secretion machinary, i.e., translocase, SecA, SecY, SecE and/or other secretion factors known to those of skill in the art are modulated in expression at an optimal ratio to SecD, SecF or SecDF. For example, it may be desired to overexpress multiple secretion factors in addition to SecDF for optimum enhancement of the secretion machinary.

The present invention also provides a method of identifying homologous non Bacillus subtilis secretion factors that comprises hybridizing part or all of secDF nucleic acid shown in FIGS. 1A–1E with nucleic acid derived from gram-positive microorganisms. In one embodiment, the nucleic acid is of genomic origin. In another embodiment, the nucleic acid is a cDNA. The present invention encompasses novel gram-positive secretion factors identified by this method.

BRIEF DESCRIPTION OF THE DRAWINGS

FIGS. 1A–1E shows the nucleic acid sequence for secDF (SEQ ID NO:1) and the deduced amino acid sequence of SecDF (SEQ ID NO:2).

FIG. 2 shows the decreased rate of processing of pre-AmyQ in SecDF mutants of *B.subtilis*. Mutant strain (MIF1) and wildtype *B. subtilis* (168) harboring a plasmid encoding AmyQ (pKTH10; Takkinen K., Pettersson R. F., Kalkkinen N., Palva I., Soderlund H., Kaariainen L. J. Biol. Chem. 258:1007–1013(1983).) were tested for precursor and mature amylase using western blot analysis:

lane 1 and 2: proteins secreted into the medium lane 3 and 4: total cell proteins analyzed.

FIGS. 3A–3B shows the expression of secDF in *B. subtilis* grown in TY medium (3A) and minimal media (3B) as measured by β-gal.

FIGS. 4A–4B show the levels of AmyQ (*Bacillus amyloliquefaciens* α-amylase) accumulated in *B.subtilis* MIF1 relative to wildtype as a measurement of the total amount of AmyQ (FIG. 4A) and as a percentage of pre-AmyQ (FIG. 4B). Data are derived from the gel analysis of FIG. 2.

FIGS. 5A and 5B show a pulse chase experiment of amylase made in wild type *B. subtilis* and *B. subtilis* MIF1 (insertional inactivation of SecDF). FIG. 5A is a 10% SDS gel with lane 2, 3 and 4 illustrating the levels of protein seen at 1', 2' and 10' in wild type *B.subtilis* and lanes 5, 6 and 7 illustrating the levels of protein seen at 1', 2' and 10' in *B. subtilis* MIF1. After pulse chase the cells were lysed and the proteins were selectively precipitated with anti-amylase antibodies. FIG. 5B shows the percentage of AmyQ precursor at chase times 1', 2', 5' and 10' of wild type *B. subtilis* and *B. subtilis* MIF1.

FIGS. 6A–6C. FIG. 6A illustrates a chromosomal organization of the *B. subtilis* secDF locus. FIG. 6B illustrates the chromosomal organization of the *E. coil* secD locus (adapted from Pogliano, et al., 1994, J. Bacteriol, 176:804–814 and Reuter et al., 1991, J. Bacterial. 173:2256–2264). FIG. 6C is a comparison of the deduced amino acid sequences of SecDF of *B.subtilis* and SecD (SEQ ID NO:3) and SecF (SEQ ID NO:4) of *E.coli*. Identical amino acids (*), or conservative replacements (.) are marked. The conserved regions D1–D6 and F1–F4, which are present in all known SecD and SecF proteins/domains are marked with black, or open bars. Putative membrane-spanning domains (I–XII) are indicated in gray shading. The membrane-spanning domains of *E.coli* SecD and SecF were adapted from Pogliano et al., 1994, J. Bacteriol. 176:804–814 and GenBank sequence ID number 134401, respectively. The membrane spanning domains in SecDF of *B.subtilis* were predicted using algorithms described by Sipos and von Heijne (Sipos et al., 1993, Eur. J. Biochem 213:1333–1340). The point of truncation of the SecDF protein in *B.subtilis* is indicated with an arrow.

FIG. 7 illustrates the growth at 15° C. as a function of time as measured at OD600 for the strains *B.subtilis* 168 pGS1 (neutral protease expression plasmid), *B.subtilis* 168 pKTH10 (amylase expression plasmid), *B.subtilis* MIF1 pKTH10 and *B.subtilis* MIF1 pGS1.

FIG. 8 illustrates the genomic map of the nucleic acid encoding secDF and surrounding nucleic acid.

FIGS. 9A–9B illustrates the restriction map of plasmids MID2 (MID2 and MID refer to the same plasmid) (9A) and MIF1 (MIF and MIF1 refer to the same plasmid) (9B) containing internal secDF fragments which have been interrupted.

FIG. 10: Demonstration that SecDF is a single protein in *B. subtilis*. A fusion was made between the ORF encoding *B. subtilis* SecDF and a c-myc polypeptide. This fusion protein was detected in a Western blot using antibodies directed to c-myc. It can be seen that a 97 kDa protein is detected corresponding to the expected size for a SecDF/myc fusion.

lane 1: overnight culture of *E. coli* (in TY) with plasmid pX-DFmyc lane 2: e overnight culture *B. subtilis* 168 DF-myc (in TY) without xylose induction lane 3: same as 2 grown with xylose induction Size markers have been given (in kDa). pX-DFmyc was obtained from Dr. W. Schumann: it is a vector that will replicate in *E.coli* and integrate in Bacillus. The secDF gene has been cloned with a myc-tag at the C-terminus of SecDF. The secDF gene is under the control of the inducible xylose promoter.

FIG. 11: Impaired extracellular accumulation of AmyQ. Cells overexpressing amylase were grown under two different conditions: at 37° C. during 1 hour and at 15° C. during 16 hours. The amount of secreted amylase was determined with Western blot analysis.

lane 1: *B. subtilis* 168 (pKTH10); medium after 1 hour growth at 37° C.

lane 2: *B. subtilis* MIF1 (pKTH10); medium after 1 hour growth at 37° C.

lane 3: *B. subtilis* 168 (pKTH10); medium after 16 hours growth at 15° C.

lane 4: *B. subtilis* MIF1 (pKTH10); medium after 16 hours growth at 15° C.

The bands have been scanned and analyzed: after 1 hour at 37 C. strain MIF1 secretes 72% compared to wildtype; after 16 hours at 15 C. MIF1 secretes only 20% compared to wild type level.

FIG. 12; Impaired secretion of neutral protease. Cells overexpressing neutral protease (from plasmid GS1) were grown under two different conditions: at 37° C. during 1 hour and at 15° C. during 16 hours. The amount of secreted neutral protease was determined with Western blot analysis.

lane 1: *B. subtilis* 168 (pGS1); medium after 1 hour growth at 37° C.

lane 2: *B. subtilis* MIF1 (pGS1); medium after 1 hour growth at 37° C.

lane 3: *B. subtilis* 168 (pGS1); medium after 16 hours growth at 15° C.

lane 4: *B. subtilis* MIF1 (pGS1); medium after 16 hours growth at 15° C.

The amounts of neutral protease have been quantified: after 1 hour at 37° C.: MIF1 secretes 47% NprE compared to wildtype; after 16 hours at 15° C.: MIF1 secretes 43% NprE compared to wildtype.

FIG. 13 shows the amino acid alignment of *E. coli* SecD (SEQ ID NO:3) with *Bacillus subtilis* SecDF (SEQ ID NO:2).

FIG. 14 shows the amino acid alignment of *E.coli* SecF (SEQ ID NO:4) with *Bacillus subtilis* SecDF (SEQ ID NO:2).

FIG. 15 shows the putative membrane-spanning domains numbered I–XIII. The positions of the patterns of conserved residues (D1–D6 and F1–F4) are indicated in bold. The carboxyl-terminus of the truncated SecDF protein of *B.subtilis* MIF is marked with and arrow. N is the amino-terminus and C is the carboxyl-terminus.

FIGS. 16A–16C. FIG. 16A shows a schematic presentation of the secDF locus of *B.subtilis* MID. By a single-crossover event (Campbell-type integration), the secDF promoter region was replaced with the Pspac promoter of the integrated plasmid pMutin2, which can be repressed by the product of the lacI gene. Simultaneously, the spoVG-lacZ reporter gene of pMutin2 was placed under the transcriptional control of the secDF promoter region. The chromosomal fragment from the secDF regions which was amplified by PCR and cloned into pMutin2, is indicated with black bars. Only the restriction sites relevant for the construction are shown. PsecDF promoter region of the secDF gene; on pBR322, replication functions of pBR322; secDF', 3' truncated secDF gene; $T_1T_2$, transcriptional terminators on pMutin2; SL, putative rho-independent terminator of secDF transcription. FIG. 16B is a schematic presentation of the secDF locus of B.subtilis MIF. The secDF gene was disrupted by the integrated plasmid pMutin2. 'secDF,5' truncated secDF gene. FIG. 16C shows the growth of secDF mutants in Ty medium at 15° C. Overnight cultures of strains grown in TY medium at 37° C. were diluted 100-fold in fresh TY medium and incubated at 15° C. Growth of B.subtilis 168 is shaded squares; 168 (pKTH10) open squares; MID closed triangle; MIDpKth10 open triangle; MIF closed circle; MIF (pKt1110) open circles in the absence of IPTG, was determined by optical density readings at 600 nm. Growth of B.subtilis MID and MID (pKTH10) open triangles was determined in medium supplemented with IPTG.

FIGS. 17A–17D shows the identification of the SecDF protein in B.subtilis. To identify the SecDF protein, cells of B.subtilis XDF-Myc, which contain the secDFmyc gene under control of a xylose-inducible promoter, were grown in the absence or presence of xylose and protoplasted. In parallel, protoplasts were incubated for 30 min without further additions, in the presence of trypsin (1 mg/ml), or in the presence of tyrpsin and Triton X-100 (1%). Samples were used for SDS-PAGE and Western blotting. FIG. 17A illustrates that SecDF-Myc was visualized with specific antibodies against the c-Myc epitope. FIG. 17B shows SipS (extracellular control) and FIG. 17C shows GroEL (cytoplasmic control) which were visualized with specific antibodies. FIG. 17D shows limited proteolysis of SecDF-Myc with trypsin (1 mg/ml) that was performed by incubation for various periods of time. Intact SecDF-Myc (82 kDa), trypsin resistant fragments of SecDF-Myc (54 kDa and 23 kDa), SipS and GroEL are indicated.

DETAILED DESCRIPTION

Definitions

As used herein, the genus Bacillus includes all members known to those of skill in the art, including but not limited to *B. subtilis, B. licheniformis, B. lentus, B. brevis, B. stearothermophilus, B. alkalophilus, B. amyloliquefaciens, B. coagulans, B. circulans, B. lautus* and *B. thuringiensis*.

The present invention encompasses novel SecD, SecF and SecDF secretion factors from any gram positive organism. In a preferred embodiment, the gram-positive organism is Bacillus. In another preferred embodiment, the gram-positive organism is from *B. subtilis*. As used herein, the phrase, "*B.subtilis* SecDF secretion factor" refers to the amino acid sequence shown in FIGS. 1A–1E as well as the amino acid sequence encoded by the nucleic acid disclosed in Kunst et al., 1997, Nature 390:249–256 (GenBank accession number ID g2635229) and GenBank accession number AF024506 and the present invention encompasses the SecDF amino acid sequence encoded by secDF nucleic acid disclosed in FIGS. 1A–1E, GenBank accession number ID g2635229 and accession number AF024506. The present invention encompasses amino acid variants of *Bacillus subtilis* that are able to modulate secretion alone or in combination with other secretions factors in gram-positive microorganisms.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof. As used herein, lower case "secDF" is used to designate a nucleic acid sequence, whereas upper case "SecDF" is used to designate an amino acid sequence. A "*B.subtilis* polynucleotide homolog" or "polynucleotide homolog" as used herein refers to a polynucleotide that has at least 80%, at least 90% and at least 95% identity to FIGS. 1A–1E or which is capable of hybridizing to part or all of the nucleic acid of FIGS. 1A–1E under conditions of high stringency and which encodes an amino acid sequence that is able to modulate secretion of the gram-positive microorganism from which it is derived. Modulate as used herein refers to the ability of a secretion factor to alter the secretion machinery such that secretion of proteins is altered.

The terms "isolated" or "purified" as used herein refer to a nucleic acid or amino acid that is removed from at least one component with which it is naturally associated.

As used herein, the term "heterologous protein" refers to a protein or polypeptide that does not naturally occur in a gram-positive host cell. Examples of heterologous proteins include enzymes such as hydrolases including proteases, cellulases, amylases, other carbohydrases, and lipases; isomerases such as racemases, epimerases, tautomerases, or mutases; transferases, kinases and phophatases. The heterologous gene may encode therapeutically significant proteins or peptides, such as growth factors, cytokines, ligands, receptors and inhibitors, as well as vaccines and antibodies. The gene may encode commercially important industrial proteins or peptides, such as proteases, carbohydrases such as amylases and glucoamylases, cellulases, oxidases and lipases. The gene of interest may be a naturally occurring gene, a mutated gene or a synthetic gene.

The term "homologous protein" refers to a protein or polypeptide native or naturally occurring in a gram-positive host cell. The invention includes host cells producing the homologous protein via recombinant DNA technology. The present invention encompasses a gram-positive host cell having a deletion or interruption of the nucleic acid encoding the naturally occurring homologous protein, such as a protease, and having nucleic acid encoding the homologous protein, or a variant thereof, re-introduced in a recombinant form. In another embodiment, the host cell produces the homologous protein.

DETAILED DESCRIPTION OF THE PREFERRED EMBODIMENTS

The present invention provides novel secretion factors and methods that can be used in gram-positive microorganisms to ameliorate the bottleneck to protein secretion and the production of proteins in secreted form, in particular when the proteins are recombinantly introduced and overexpressed by the host cell. The present invention provides the secretion factor SecDF derived from *Bacillus subtilis* and illustrates that interruption of the nucleic acid encoding SecDF via homologous recombination results in a loss in the host cell's capacity to process and secrete a recombinantly introduced heterologous pro-protein.

I. SecDF Nucleic Acid and Amino Acid Sequences

Nucleic Acid Sequences

The secDF polynucleotide having the sequence as shown in FIGS. 1A–1E and in Kunst et al., 1997, Nature 390:249–256 (GenBank accession number ID g2635229) encodes the *Bacillus subtilis* secretion factor SecDF. The *Bacillus subtilis* SecDF was initially identified via a FASTA search of *Bacillus subtilis* translated genomic sequences.

The SecD and SecF portions of SecDF of FIGS. 1A–1E (see also FIGS. 13 and 14) were found to have 29% and 28% identity to *E.coli* SecD and SecF, respectively. Subsequent to Kunst et al., the *B.subtilis* nucleic acid sequence was confirmed and has been submitted to GenBank database with accession number AF024506. The present invention encompasses secDF nucleic acid disclosed in FIGS. 1A–1E, GenBank accession number ID g2635229 and accession number AF024506.

The present invention provides secD polynucleotide, secF polynucleotide and secDF polynucleotide which may be used alone or together in a host cell. The polynucleotide sequences for SecD and SecF portions of SecDF can be determined from FIGS. 13 and 14 which show the amino acid alignment of *E. coli* SecD and SecF with the *Bacillus subtilis* SecDF.

In contrast to *E.coli* secretion factors SecD and SecF and as illustrated in FIG. 6, *Bacillus subtilis* SecDF is encoded by one polynucleotide. The SecD operon of *E.coli* consists of the YahC, secD and secF genes (Pogliano et al., 1994, J. Bacteriol. 176:804–814). This function-related operon structure is not conserved in *B.subtilis*, as the yajC-like gene yrbF and secDF are separated by two pairs of divergently transcribed genes, denoted yrzE, yrbG, spoVB and yrzD.

The present invention encompasses secD, secF and secDF polynucleotide homologs encoding gram-positive secretion factors SecD, SecF and SecDF, respectively, whether encoded by one or multiple polynucleotides which have at least 80%, or at least 90% or at least 95% identity to *B. subtilis* SecD, SecF and SecDF, respectively as long as the homolog encodes a protein that is able to function by modulating secretion in a gram-positive microorganism. As will be understood by the skilled artisan, due to the degeneracy of the genetic code, a variety of polynucleotides, i.e., secD, secF and secDF polynucleotide variants, can encode the *Bacillus subtilis* secretion factors SecD, SecF and SecDF. The present invention encompasses all such polynucleotides.

Gram-positive microorganism polynucleotide homologs of *B. subtilis* secD, secF and secDF secretion factors can be identified through nucleic acid hybridization of gram-positive microorganism nucleic acid of either genomic of cDNA origin. The polynucleotide homolog sequence can be detected by DNA-DNA or DNA-RNA hybridization or amplification using probes, portions or fragments disclosed in FIGS. 1A–1E. Accordingly, the present invention provides a method for the detection of secD, secF and secDF polynucleotide homologs which comprises hybridizing a nucleic acid sample with part or all of a nucleic acid sequence from secD, secF or secDF.

Also included within the scope of the present invention are secDF, secD and secF polynucleotide sequences that are capable of hybridizing to part or all of the secDF nucleotide sequence of FIGS. 1A–1E under conditions of intermediate to maximal stringency. Hybridization conditions are based on the melting temperature (Tm) of the nucleic acid binding complex, as taught in Berger and Kimmel (1987, *Guide to Molecular Cloning Techniques*, Methods in Enzymology, Vol 152, Academic Press, San Diego Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The term "hybridization" as used herein shall include "the process by which a strand of nucleic acid joins with a complementary strand through base pairing" (Coombs J (1994) *Dictionary of Biotechnology*, Stockton Press, New York N.Y.). The process of amplification as carried out in polymerase chain reaction (PCR) technologies is described in Dieffenbach C W and G S Dveksler (1995, *PCR Primer a Laboratory Manual*, Cold Spring Harbor Press, Plainview N.Y.). A nucleic acid sequence of at least about 10 nucleotides and as many as about 60 nucleotides from the secDF nucleotide sequence of FIGS. 1A–1E, preferably about 12 to 30 nucleotides, and more preferably about 20–25 nucleotides can be used as a probe or PCR primer.

Amino Acid Sequences

The *B. subtilis* secDF polynucleotide as shown in FIGS. 1A–1E encodes *B. subtilis* SecDF. The *B.subtilis* secDF gene specifies one protein of 737 residues with a calculated molecular mass of 81,653. The SecDF protein has a two-domain structure, consisting of an amino-terminal SecD domain (about 416 residues) and a carboxyl-terminal SecF domain (291 residues). These domains show significant sequence similarity to known SecD and SecF proteins from other organisms, the highest similarity being found with SecD and SecF proteins from the cyanobacterium Synechocystis. The stretch of 30 residues which links the SecD and SecF domains of *B.subtilis* SecDF is not conserved in other known SecD or SecF proteins. The corresponding domains of SecDF also show sequence similarity among themselves, in particular at their carboxyl-termini (22% identical residues and 44% conservative replacements in a stretch of 200 residues). *B.subtilis* SecDF shows amino acid sequence similarity to solute transporters, such as AcrF of *E.coli* (42% identical residues and conservative replacements in a stretch of 253 residues) which is involved in acriflavine resistance (GenBank sequence ID number g399429) and ActII-3 of *Streptomyces coelicolor* (46% identical residues and conservative replacements in a stretch of 159 residues) which is involved in the transport of antibiotics (GenBank sequence ID number g80715).

Alignment of *B.subtilis* SecDF with the SecD and SecF proteins from the organisms listed in Table I revealed that these proteins do not show similarity over their entire length. Ten short patterns of conserved amino acids were identified, which are present in all known SecD and SecF proteins. As shown in FIG. 6C, these conserved regions were named D1–D6 and F1–F4 for the SecD and SecF domains/proteins, respectively. The positions of these conserved regions are indicated in FIG. 6C. Some of these conserved domains are present in both SecD and SecF. This similarity is most obvious for the regions D1 and F1 which, respectively, have the consensus sequence G(L/I)DLRGG and G(L/I)DF(A/T)GG. Parts of the conserved regions D5 and F2 also show similarity.

The present invention encompasses gram positive microorganism amino acid variants of the amino acid sequence shown in FIGS. 1A–1E that are at least 80% identical, at least 90% identical and at least 95% identical to the sequence shown in FIGS. 1A–1E as long as the amino acid sequence variant is able to function by modulating secretion of proteins in gram-positive microorganisms.

TABLE I

Percentage of identical residues plus conservative replacements in SecD and SecF domains and proteins from various organisms.

| Organism | SecD | SecF |
| --- | --- | --- |
| B. subtilis | 100 | 100 |
| E. coli | 47 | 51 |
| H. influenzae | 48 | 52 |
| H. pylori | 45 | 49 |
| M. jannaschii | 39 | 39 |
| M. tuberculosis | 45 | 52 |
| R. capsulatus | 47 | 50 |
| S. coelicolor | 42 | 57 |
| Synechocystis sp. | 49 | 56 |

The GenBank sequence ID numbers are: SecD (*E. coli*) 134399; SecF (*E. coli*) 134401; SecD (*Huemophilus influenzae*) 1173414; SecF (*H. influenzae*) 1173416; SecD (*Helicobacter pylori*) 2314730; SecF (*H. pylori*) 2314729; SecD (*Methanococus jannaschii*) 2129225: SecF (*M. jannaschii*) 2129224; SecD (*Mycobacterium tuberculosis*) 2498898; SecF (*M. tuberculosis*) 2498900; SecD (*Rhodobacter capsulatus*) 2252773; SecF (*R. capsulatus*) 2252774; SecD (*S. coelicolor*) 1076081; SecF (*S. coelicolor*) 1076082; SecD (Synechocystis sp.) 1001493; SecF (Synechocystis sp.) 1001494.

II. Expression Systems

The present invention provides expression systems for the enhanced production and secretion of desired heterologous or homologous proteins in gram-positive microorganisms.

a. Coding Sequences

In the present invention, the vector comprises at least one copy of nucleic acid encoding a gram-positive microorganism SecD, SecF, or SecDF secretion factor and preferably comprises multiple copies. In a preferred embodiment, the gram-positive microorganism is Bacillus. In another preferred embodiment, the gram-positive microorganism is *Bacillus subtilis*. In a preferred embodiment, polynucleotides which encode *B. subtilis* SecF, SecD and/or SecDF, or fragments thereof, or fusion proteins or polynucleotide homolog sequences that encode amino acid variants of SecD, SecF and/or SecDF, may be used to generate recombinant DNA molecules that direct the expression of SecD, SecF, SecDF, or amino acid variants thereof, respectively, in gram-positive host cells. In a preferred embodiment, the host cell belongs to the genus Bacillus. In another preferred embodiment, the host cell is *B.subtilis*.

As will be understood by those of skill in the art, it may be advantageous to produce polynucleotide sequences possessing non-naturally occurring codons. Codons preferred by a particular gram-positive host cell (Murray E et al (1989) Nuc Acids Res 17:477–508) can be selected, for example, to increase the rate of expression or to produce recombinant RNA transcripts having desirable properties, such as a longer half-life, than transcripts produced from naturally occurring sequence.

Altered gram positive secD, secF or secDF polynucleotide sequences which may be used in accordance with the invention include deletions, insertions or substitutions of different nucleotide residues resulting in a polynucleotide that encodes the same or a functionally equivalent SecD, SecF or SecDF homolog, respectively. As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring gram positive secD, secF or secDF.

As used herein "substitution" results from the replacement of one or more nucleotides or amino acids by different nucleotides or amino acids, respectively.

The encoded protein may also show deletions, insertions or substitutions of amino acid residues which produce a silent change and result in a functionally equivalent gram-positive SecD, SecF or SecDF variant. Deliberate amino acid substitutions may be made on the basis of similarity in polarity, charge, solubility, hydrophobicity, hydrophilicity, and/or the amphipathic nature of the residues as long as the variant retains the ability to modulate secretion. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

The secD, secF or secDF polynucleotides of the present invention may be engineered in order to modify the cloning, processing and/or expression of the gene product. For example, mutations may be introduced using techniques which are well known in the art, eg, site-directed mutagenesis to insert new restriction sites, to alter glycosylation patterns or to change codon preference, for example.

In one embodiment of the present invention, a secDF, secD or secF polynucleotide may be ligated to a heterologous sequence to encode a fusion protein. A fusion protein may also be engineered to contain a cleavage site located between the secDF nucleotide sequence and the heterologous protein sequence, so that the SecDF protein may be cleaved and purified away from the heterologous moiety.

b. Vector Sequences

Expression vectors used in expressing the secretion factors of the present invention in gram-positive microorganisms comprise at least one promoter associated with a secretion factor selected from the group consisting of SecD, SecF and SecDF, which promoter is functional in the host cell. In one embodiment of the present invention, the promoter is the wild-type promoter for the selected secretion factor and in another embodiment of the present invention, the promoter is heterologous to the secretion factor, but still functional in the host cell.

Additional promoters associated with heterologous nucleic acid encoding desired proteins or polypeptides may be introduced via recombinant DNA techniques. In one embodiment of the present invention, the host cell is capable of overexpressing a heterologous protein or polypeptide and nucleic acid encoding one or more secretion factor(s) is(are) recombinantly introduced. In one preferred embodiment of the present invention, nucleic acid encoding the secretion factor is stably integrated into the microorganism genome. In another embodiment, the host cell is engineered to overexpress a secretion factor of the present invention and nucleic acid encoding the heterologous protein or polypeptide is introduced via recombinant DNA techniques. The present invention encompasses gram-positive host cells that are capable of overexpressing other secretion factors known to those of skill in the art, including but not limited to, SecA, SecY, SecE or other secretion factors known to those of skill in the art or identified in the future.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the gram-positive host which allows for ease of selection of those hosts containing the vector. Examples of such selectable markers include but are not limited to antibiotics, such as, erythromycin, actinomycin, chloramphenicol and tetracycline.

c. Transformation

In one embodiment of the present invention, nucleic acid encoding one or more gram-positive secretion factor(s) of the present invention is introduced into a gram-positive host cell via an expression vector capable of replicating within the host cell. Suitable replicating plasmids for Bacillus are described in Molecular Biological Methods for Bacillus, Ed. Harwood and Cutting, John Wiley & Sons, 1990, hereby expressly incorporated by reference; see chapter 3 on plasmids. Suitable replicating plasmids for *B. subtilis* are listed on page 92.

In another embodiment, nucleic acid encoding one or more gram positive secretion factor(s) of the present invention are stably integrated into the microorganism genome. Preferred gram-positive host cells are from the genus Bacillus. Another preferred gram-positive host cell is *B. subtilis*. Several strategies have been described in the literature for the direct cloning of DNA in Bacillus. Plasmid marker rescue transformation involves the uptake of a donor plasmid by competent cells carrying a partially homologous resident plasmid (Contente et al., *Plasmid* 2:555–571 (1979); Haima et al., *Mol. Gen. Genet.* 223:185–191 (1990); Weinrauch et al., *J. Bacteriol.* 154(3):1077–1087 (1983); and Weinrauch et al., *J. Bacteriol.* 169(3):1205–1211 (1987)). The incoming donor plasmid recombines with the homologous region of the resident "helper" plasmid in a process that mimics chromosomal transformation.

Transformation by protoplast transformation is described for *B. subtilis* in Chang and Cohen, (1979) Mol. Gen. Genet 168:111–115; for *B.megaterium* in Vorobjeva et al., (1980) FEMS Microbiol. Letters 7:261–263; for *B. amyloliquefaciens* in Smith et al., (1986) Appl. and Env. Microbiol. 51:634; for *B.thuringiensis* in Fisher et al., (1981) Arch. Microbiol. 139:213–217; for *B.sphaericus* in McDonald (1984) J. Gen. Microbiol. 130:203; and *B.larvae* in Bakhiet et al., (1985) 49:577. Mann et al., (1986, Current Microbiol. 13:131–135) report on transformation of Bacillus protoplasts and Holubova, (1985) Folia Microbiol. 30:97) disclose methods for introducing DNA into protoplasts using DNA containing liposomes.

III. Identification of Transformants

Although the presence/absence of marker gene expression suggests that the gene of interest is also present, its presence and expression should be confirmed. For example, if the nucleic acid encoding a secretion factor is inserted within a marker gene sequence, recombinant cells containing the insert can be identified by the absence of marker gene function. Alternatively, a marker gene can be placed in tandem with nucleic acid encoding the secretion factor under the control of a single promoter. Expression of the marker gene in response to induction or selection usually indicates expression of the secretion factor as well.

Alternatively, host cells which contain the coding sequence for a secretion factor and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the secDF polynucleotide sequence can be detected by DNA-DNA or DNA-RNA hybridization or amplification using probes, portions or fragments disclosed in FIGS. 1A–1E.

IV. Secretion Assays

Means for determining the levels of secretion of a heterologous or homologous protein in a gram-positive host cell and detecting secreted proteins include, using either polyclonal or monoclonal antibodies specific for the protein. Examples include enzyme-linked immunosorbent assay (ELISA), radioimmunoassay (RIA) and fluorescent activated cell sorting (FACS). These and other assays are described, among other places, in Hampton R et al (1990, *Serological Methods, a Laboratory Manual*, APS Press, St Paul Minn.) and Maddox DE et al (1983, J Exp Med 158:1211).

A wide variety of labels and conjugation techniques are known by those skilled in the art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 and incorporated herein by reference.

V. Purification of Proteins

Gram positive host cells transformed with polynucleotide sequences encoding heterologous or homologous protein may be cultured under conditions suitable for the expression and recovery of the encoded protein from cell culture. The protein produced by a recombinant gram-positive host cell comprising a secretion factor of the present invention will be secreted into the culture media. Other recombinant constructions may join the heterologous or homologous polynucleotide sequences to nucleotide sequence encoding a polypeptide domain which will facilitate purification of soluble proteins (Kroll D J et al (1993) DNA Cell Biol 12:441–53).

Such purification facilitating domains include, but are not limited to, metal chelating peptides such as histidine-tryptophan modules that allow purification on immobilized metals (Porath J (1992) Protein Expr Purif 3:263–281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein can be used to facilitate purification.

EXAMPLE I

Example I Gives Materials and Methods for the Examples a. Plasmids, bacterial strains and media Table II lists the plasmids and bacterial strains used herein. TY medium contained Bacto tryptone (1%), Bacto yeast extract (0.5%) and NaCl (1%). S7 media 1 and 3, for the pulse-labeling of B. subtilis were prepared as described in van Diji et al. (1991, J. Gen. Microbiol. 137:2073–2083) with the exception that glucose was replaced by maltose. Minimal medium (GCHE medium; Kunst et al (1995, J. Bacteriol. 177: 2403–2407) contained glucose (1%), potassium L-glutamate (0.2%), potassium phosphate buffer (100 mM; pH 7), trisodium citrate (3 mM), $MgSO_4$ (3 mM), ferric ammonium citrate (22 mg/1), casein hydrolysate (0.1%), and L-tryptophan (50 mg/l). Antibiotics were used in the following concentrations: chloramphenicol, 5 μg/ml; erythromycin, 1 μg/ml; kanamycin, 10 μg/ml; ampicillin, 50 μg/ml. IPTG was used at 1 mM.

b. DNA techniques

Procedures for DNA purification, restriction, ligation, agarose gel electrophoresis and transformation of competent E. coli DH5α cells were carried out as described in Sambrook (1989, Molecular cloning: a Laboratory Manual, Cold Spring Harbor Laboratory Press, Cold Spring Harbor, N.Y., USA). Enzymes were from Boehringer (Mannheim, Germany). B. subtilis was transformed by adding DNA to cells growing in GCHE medium at the end of the exponential growth phase, and continued incubation for 3–4 hours. PCR was carried out with Vent DNA polymerase (New England Biolabs, Beverly, Mass.), using buffers of the supplier. The nucleotide sequences of primers used for PCR (5'-3') are listed below; nucleotides identical to genomic template DNA are printed in capital letters and restriction sites used for cloning are underlined. DNA sequences were determined using the didioxy chain-termination procedure (Laemmli 1970, Nature, 227:680–685).

To verify the previously reported sequence of the B. subtilis secF gene (Kunst 1997 supra), a plasmid (pSecDF) was constructed by inserting a DNA fragment containing the entire secDF gene, amplified by PCR with the primers AB34secd (aaaagcttAAGGGAGGATATACATAATG), SEQ ID NO: 5, and AB37secd (aaggatcc GCGTATGTCATTATAGC), SEQ ID NO: 6, into the HindIII and BamHI restriction sites of the phagemid pBluescript II+.

To construct B. subtilis MIF an internal fragment of the secDF gene (417 nucleotides) was amplified by PCR with the oligonucleotides AB32secF (aa aagcttCGACAGAGCAAGTTGAG), SEQ ID NO: 7, and AB33secF (aaggatccGATTGTATCGTTAATGG), SEQ ID NO: 8, and, subsequently, cloned into pMutin2, which resulted in plasmid pMIF. To construct B. subtilis MID a fragment containing the ribosome binding site, start codon and the first 879 nucleotides of the secDF gene, but not the secDF promoter(s), was amplified with the primers AB34secD (see above) and AB31secD (aa ggatccGTGTAATGTAGATATAAAC), SEQ ID NO: 9, and cloned into pMutin2, resulting in plasmid pMID. B. subtilis MIF and MID were obtained by Campbell type integration of plasmids pMIF and PMID, respectively, into the chromosome of B. subtilis 168. Correct integration of plasmids in the chromosome of B. subtilis was verified by Southern hybridization. To construct B. subtilis XDF-Myc the entire secDF gene was amplified by PCR with the primers AB47secD (aatctagaAAGGGAGGATATACATAATG), SEQ ID NO: 10, and AB46mycF (aggatcc ttagttcaaatcttcctcactgatcaatttctgTTCTTGCGCCGAATCTT-TTTTCAG), SEQ ID NO: 11; the sequence specifying the human c-Myc epitope is indicated in bold). The resulting PCR product, which contains the secDFmyc gene, was cleaved with XbaI and BamHI, and ligated into the SpeI and BamHI sites of pX. This resulted in plasmid pXDFmyc, which contains the secDFmyc gene under the transcriptional control of the xylose-inducibie xylA promoter. Upon transformation of B. subtilis 168 with pXDFmyc, both the xylA promoter and secDFmyc were integrated into the chromosomal amyE gene, resulting in B. subtilis XDF-Myc. The disruption of the amyE gene was confirmed by growing B. subtilis XDF-Myc on TY plates containing 1% starch and subsequent exposure of the plates to iodine. As shown by a lack of halo formation, B. subtilis XDF-Myc did not secrete active α-amylase.

c. Pulse-chase protein labeling, immunoprecipitation

SDS-PAGE and fluorography-Pulse-chase labeling experiments with B. subtilis and immunoprecipitations were performed as described in van Dijl et al., 1991, J. Gen. Microbiol 137:2073–2083. SDS-PAGE was performed according to Laemmli (1970, Nature 227:680–685). [$^{14}$C]-methylated molecular weight markers were from Amersham (Little Chalfont, UK). Fluorography was performed with Autofluor (National Diagnostics, Atlanta, Ga., USA). Relative amounts of precursor and mature forms of secreted proteins were estimated by scanning of autoradiographs with an LKB ultrascan XL laser densitometer (LKB, Bromma, Sweden).

d. Western blot analysis

Western blotting was performed using a semi-dry system as described in Miller supra. After separation by SDS-PAGE, proteins were transferred to Immobilon-PVDF membranes (Millipore Corp., Bedford, Mass.) Proteins were visualized with specific antibodies and horseradish peroxidase (HRP) anti-rabbit or anti-mouse IgG conjugates, using the ECL detection system of Amersham. Streptavidin-IIRP conjugate was obtained from Amersham.

e. Protease accessibility

Protoplasts were prepared from exponentially growing cells of B. subtilis. To this purpose cells were concentrated 5-fold in protoplast buffer (20 mM potassium phosphate, pH 7.5; 15 mM $MgCl_2$; 20% sucrose) and incubated for 30 min in the presence of 1 mg/ml lysozyme (37° C.). Next, the protoplasts were collected by centrifugation and resuspended in fresh protoplast buffer. The protease accessibility of membrane proteins was tested by incubating the protoplasts at 37° C. in the presence of 1 mg/ml trypsin (Sigma Chemical Co., St. Louis, Mo., USA) for various periods of time. The reaction was terminated by the addition of 1.2 mg/ml trypsin inhibitor (Sigma Chemical Co.). Finally, protoplasts were collected by centrifugation, and the degradation of specific proteins was analyzed by SDS-PAGE and Western-blotting. In parallel, protoplasts were incubated without trypsin, or in the presence of trypsin and 1% Triton X-100. Samples containing TX-100 were directly used for SDS-PAGE after the addition of trypsin inhibitor.

f. β-Galactosidase activity

Overnight cultures were diluted 100-fold in fresh medium and samples were taken at hourly intervals for optical density (OD) readings at 600 nm and β-Galactosidase activity determinations. The β-Galactosidase assay and the calculation of β-Galactosidase units (per OD600) were performed as described in Miller, 1982, Experiments in Molecular Genetics, Cold Spring Harbor Laboratory Press, Cold Spring Harbor, N.Y., USA.

TABLE II

Plasmids and Bacterial Strains

| Strain/Plasmid | Genotype/Properties | Source/Reference |
|---|---|---|
| Strains | | |
| *E. coli* | | |
| DH5α | F80dlacZ-M15 endAl recAl hsdR17($r_k^-$ $m_k^-$) thi-I gyrA96 relAl-(lacZYA-argF) U169 | Bethesda Research Laboratories |
| *B. subtilis* | | |
| 168 | trpC2 | Kunst et al (supra) |
| MIF | trpC2; secDF::pMIF; Em$^r$ | Examples |
| MID | trpC2; secDF::pMID; Em$^r$ | Examples |
| XDF-Myc | trpC2; amyE::xylA-secDFmyc; Cm$^r$ | Examples |
| Plasmids | | |
| pBluescript II KS+ | | 10 cloning vector; Ap$^r$ Stratagene |
| pSecDF | | pBluescript II KS+ derivative, carries the secDF gene; *B Subtilis* Examples |
| pX | | vector for the integration of genes in the amyE locus of *B. subtilis*; integrated genes will be transcribed from the xylA promoter; carries the xylR gene; Ap$^r$; Cm$^r$ Kim et al. 1996, Gene 181: 71–76 |
| pXDFmyc | | pX derivative; carries the *B. subtilis* secDF-myc gene downstream of the xylA promoter Examples |
| pMutin2 | | pBR322-based integration vector for *B. subtilis*; contains a multiple cloning site downstream of the Ehrlich Pspac promoter and a promoterless lacZ gene preceded by the ribosome-binding site of the spoVG gene; Ap$^r$; Em$^r$ V. Vagner and S. D. (Yansura et al., 1984, Genetics and Biochemistry of Bacilli pp. 249–263 Academic Press, Orlando, USA) |
| pMIF | | pMutin2 derivative; carries an internal fragment of the secDF gene Examples |
| pMID | | pmutin2 derivative; carries the 5' part of the secDF gene *B. subtilis* Examples |
| pKTH10 | | Contains the amyQ gene of *B. amyloliquefaciens*; Km$^r$ Palva, 1982, Gene 19:81–87 |
| pKTH10-BT | | pKTH10 derivative, encodes the AmyQ-PSBT fusion protein Tjalsma et al. 1998 |

EXAMPLE II

This Example describes the membrane topology of *Bacillus subtilis* SecDF. Algorithms described by Sipos and von Heijne (Sipos et al.,1993, Eur. J. Biochem 213:1333–1340) predict that the SecDF (Bsu) protein has twelve membrane-spanning domains, the amino- and carboxyl-termini being localized in the cytoplasm. Two large extracellular loops are localized between the first and second, and the seventh and eighth membrane-spanning domains, respectively (FIG. 15). These predictions are in good agreement with the topology models proposed for SecD and SecF of *E. coli*, in which both SecD and SecF have six membrane-spanning domains with large periplasmic loops being located between the first and second membrane-spanning domains (Pogliano, 1994, supra).

To verify the predicted cytoplasmic localization of the carboxyl-terminus of SecDF, we studied the protease-accessibility of SecDF-Myc in protoplasts. As shown by Western blotting, two trypsin-resistant SecDF-Myc-derived fragments of about 54 kDa and 23 kDa were detectable upon incubation of intact protoplasts of xylose-induced *B. subtilis* XDF-Myc cells with trypsin. Under the same conditions, the *B. subtilis* signal peptidase SipS, of which a large part is exposed to the external side of the membrane (van Dijl et al, EMBO J. 11:2819–2828), was completely degraded by trypsin, whereas the cytoplasmic protein GroEL remained unaffected. In contrast, both SecDF-Myc-derived fragments and GroEL were completely degraded by trypsin when protoplasts were lysed by the addition of 1% Triton X-100. Taken together, these findings show that the carboxyl-terminus of SecDF-Myc is protected against trypsin in intact protoplasts, suggesting that the carboxyl-terminus of *B.subtilis* SecDF is localized in the cytoplasm.

To study the kinetics of the formation of the two trypsin-resistant SecDF-Myc-derived fragments, limited proteolysis experiments were performed in which protoplasts of xylose-induced *B. subtilis* XDF-Myc cells were incubated with trypsin for various periods of time. As shown by Western blotting, the 54 kDa fragment is a transiently existing intermediate product in the degradation of intact SecDF-Myc to the trypsin-resistant 23 kDa fragment. As judged from the apparent molecular masses of the trypsin-resistant fragments, it is most likely that trypsin cleavage of SecDF-Myc occurs in the two predicted extracellular domains between the first and second membrane-spanning domains, and the seventh and eighth membrane-spanning domains.

EXAMPLE III

This Example relates to the cold-sensitive growth of *B.subtilis* secDF mutants. To analyze the effects of SecDF depletion on cell growth and protein secretion, two mutant *B. subtilis* strains were constructed with the integrative plasmid pMutin2 (provided by V. Vagner and S. D. Ehrlich, INRA, Jouy en Josas, France). In the first strain, denoted *B. subtilis* MID, the encoding sequence of the secDF gene was left intact, but the secDF promoter was replaced with the IPTG-inducible Pspac promoter, present on pMutin2; in the second strain, denoted *B. subtilis* MIF, the coding sequence of the SecDF gene was disrupted with pMutin 2 (FIGS. 16A and 16B, respectively). The point of truncation of the SecDF protein of *B. subtilis* MIF is indicated in FIG. 6C. Irrespective of the growth medium used or the presence of IPTG, both *B. subtilis* MID and MIF showed growth rates at 37° C. similar to that of the parental strain *B. subtilis* 168, demonstrating that under these conditions SecDF was not essential for growth and viability of the cells. By contrast, SecDF was important for growth in TY medium at 15° C.: compared to the growth of the parental strain (FIG. 16C, indicated by the closed square), the growth of *B. subtilis* MID (in the absence of IPTG) and *B. subtilis* MIF was significantly reduced. In fact, the growth rates of the two latter strains were reduced to the same extent (FIG. 16C, indicated by the closed triangle and circle respectively) and, in addition, the cells of both strains showed a filamentous morphology. Growth of *B. subtilis* MID AT 15° C. could be restored by the addition of IPTG to the growth medium (FIG. 16C, indicated with the closed triange), though not completely to wild-type levels. Similarly, growth of *B. subtilis* MIF at 15° C. could be restored to a similar level as that of *B. subtilis* MID in the presence of IPTG, by introducing the secDF-myc gene in the amyE locus, indicating the c-Myc tag did not interfere with SecDF function. Interestingly, the growth defects of *B. subtilis* MID (in the absence of IPTG) and MIF were not observed instantaneously upon incubation at 15° C., as both strains showed growth rates comparable to those of the parental strain until the mid-exponential growth phase (OD600=0.3–0.4; FIG. 16C).

To test whether SecDF might be even more important for growth under conditions of hyper-secretion, the *B. subtilis* MID and MIF strains were transformed with plasmid pKTH10, which results in the secretion of the *Bacillus amyloliquefaciens* α-amylase AmyQ at high levels (≈1.3 g/l; Kontinen et al., 1988, J. Gen Microbiol, 134:2333–2344 and Palva, 1982, Gene 19:81–87). Irrespective of the presence of pKTH10, growth of *B. subtilis* MID and MIF at 37° C. was not affected. In contrast, at 15° C. *B. subtilis* MID (in the absence of IPTG) and MIF cells transformed with pKTH10 completely stopped growing after reaching the mid-exponential growth phase and, subsequently, cells even started to lyse (FIG. 16C, indicated with the open triangle and circle, respectively). The latter observation showed that the cold-sensitive phenotype of cells depleted of SecDF was exacerbated by high levels of AmyQ secretion. The presence of pKTH10 did not affect the growth at 15° C. of either the parental strain, or *B. subtilis* MID in the presence of IPTG (FIG. 16C, indicated with the open triangle), showing that high-level secretion of AmyQ per se did not affect the growth of *B. subtilis* at low temperature. Taken together, these observations show that the *B.subtilis* SecDF (Bsu) protein is required for efficient growth at low temperatures, in particular under conditions of high-level protein secretion.

EXAMPLE IV

This Example demonstrates that SecDF is required for efficient secretion of AmyQ. To investigate the importance of SecDF for protein secretion at moderate levels (about 30 mg of protein per liter), the secretion of the neutral protease NprE by *B. subtilis* MIF was analyzed by Western blotting. Both at 37° C. and 15° C., the absence of SecDF did not result in the accumulation of pre-NprE, and similar amounts of mature NprE were detected in the medium of *B. subtilis* MIF and the parental strain.

To evaluate the importance of SecDF under conditions of hyper-secretion, the secretion of AmyQ into the growth medium was investigated by Western blotting experiments. The results showed that *B. subtilis* MIF (pKTH10) secreted reduced levels of AmyQ into the culture medium. This was most clearly observed with cells in the transition phase between exponential and post-exponential growth, which had been washed and resuspended in fresh medium. If the washed cells were incubated for 1 hour at 37° C., the medium of *B. subtilis* MIF contained about 65%±10% of the amount of AmyQ secreted by the parental strain. An even more drastic effect was observed at 15° C.; after 16 hours of incubation, the medium of *B. subtilis* MIF contained about 40%±10% of the amount of AmyQ secreted by the parental strain. The reduced secretion of AmyQ into the medium by *B. subtilis* MIF was paralleled by an increased accumulation of pre-AmyQ in the cells. Since the cellular levels of mature AmyQ were not affected in the absence of intact SecDF, these data suggest that SecDF is required for the efficient translocation of pre-AmyQ, but not the release of mature AmyQ from the membrane.

To investigate the important of SecDF for the translocation of pre-AmyQ, *B. subtilis* MIF was transformed with plasmid pKTH10-BT$^2$, which specifies a hybrid AmyQ protein containing the biotin-accepting domain (PSBT) of a transcarboxylase from *Propionibacterium shermannii* (Jander et al., 1996, J. Bacteriol. 178:3049–3058) fused to its carboxyl-terminus. The rationale of this experiment is that pre-AmyQ-PBST will only be biotinylated by the cytoplasmic biotin-ligase if the rate of translocation of pre-AmyQ-PSBT is slowed down to such an extent that the PSBT-domain can fold into its native three-dimensional structure and accept biotin before transport across the membrane.

To investigate the importance of SecDF for the translocation of pre-AmyQ, *B. subtilis* MIF was transformed with plasmid pKTH10-BT$^2$, which specifies a hybrid AmyQ protein containing the biotin-accepting domain (PSBT) of a transcarboxylase from *Propionibacterium shermannii* (Jander, supra) fused to its carboxyl-terminus. The rationale of this experiment is that pre-AmyQ-PSBT will only be biotinylated by the cytoplasmic biotin-ligase if the rate of translocation of pre-AmyQ-PSBT is slowed down to such an extent the PSBT-domain can fold into its native three-dimensional structure and accept biotin before transport across the membrane. Cells lacking intact SecDF accumulate biotinylated pre-AmyQ-BT, whereas no biotinylated (pre-)AmyQ-PSBT was detected in cells of the parental strain of *B. subtilis* XDF-Myc, which were transformed with pKTH10-BT. These finds show that the rate of translocation of pre-AmyQ-PSBT is significantly reduced in cells lacking SecDF.

To determine the rate of pre-AmyQ translocation in the absence of SecDF, the kinetics of pre-AmyQ processing by signal peptidase were studied by pulse-chase labeling of *B. subtilis* MIF containing pKTH10. Even at 37° C. the rate of pre-AmyQ processing was decreased in cells lacking an intact SecDF gene; after a chase of 1 min, about 32% of the labeled AmyQ was mature in *B. subtilis* MIF whereas, under the same conditions, about 59% of the AmyQ was mature in the parental strain. The effects of the absence of intact SecDF were even more pronounced at 23° C.; after a chase of 4 min, mature AmyQ was hardly detectable in *B. subtilis* MIF whereas, under the same conditions, about 40% of the labeled AmyQ was mature in the parental strain.

Pulse-chase labeling experiments were also performed with *B. subtilis* XDF-Myc, which overproduces the SecDF-Myc protein upon induction with xylose. Overproduction of SecDF-Myc did not significantly influence the rate of pre-AmyQ processing, showing that wild-type levels of SecDF are not limiting for the translocation of pre-AmyQ and that overproduction of SecDF-myc does not interfere with normal SecDF function.

EXAMPLE V

This example describes the growth phase and medium-dependent transcription of the secDF gene. To test whether the transcription of the secDF gene depends on the growth phase or medium composition, as previously shown for the signal peptidase-encoding genes sipS and sipT (Bolhuis et al., 1996, Mol. Microbiol. 22:605–618 and Tjalsma, 1997, J. Biol. Chem., 272: 25983–25992), we made use of the transcriptional secDF-lacZ gene fusions present in *B. subtilis* MID and MIF. *B.subtilis* MIF was grown in three different media (minimal medium, TY, or TY supplemented with 1% glucose), and samples withdrawn at hourly intervals were assayed for β-galactosidase activity. Nearly constant levels of β-galactosidase activity were observed during growth in minimal medium, suggesting that the secDF gene was expressed constitutively. In contrast, cells grown in TY medium showed increasing levels of β-galactosidase activity during exponential growth, with a maximum at the beginning of the stationary phase. The β-galactosidase activity decreased in the post-exponential growth phase suggesting that secDF promoter activity was highest in the transition phase between the exponential and post-exponential growth phase. The addition of 1% glucose to TY medium caused a drastic increase in the β-galactosidase levels of cells in the post-exponential growth phase, showing that glucose strongly stimulates the transcription of the secDF gene. Taken together, these findings show that the transcription levels of the secDF gene depend on the growth phase and growth medium

EXAMPLE VI

This Example illustrates that secDF encodes one protein. To show that the secDF gene encodes only one protein of approximately 82 kDa, the 3' end of the secDF gene was extended with 11 codons, specifying the human c-Myc epitope (EQKLISEEDLN; Evan et al., 1985, Mol. Cell. Biol. 5: 3610–3616). Next, the myc-tagged secDF gene (secDF-myc) was placed under the transcriptional control of the xylose-inducible xylA promoter and, subsequently, integrated via a double-crossover replacement recombination into the amyE locus of *B. subtilis*, using the pX system developed by Kim et al. (1996, Gene 181:71–76). The resulting strain was named *B. subtilis* XDF-Myc. As shown by Western blotting and subsequent immuno-detection with c-Myc-specific monoclonal antibodies, the SecDF-Myc protein was produced in *B. subtilis* XDF-Myc cells growing in TY medium supplemented with 1% xylose, but not in cells growing in TY medium lacking xylose. Similar results were obtained if samples for Western blotting were prepared from intact cells or protoplasts of *B. subtilis* XDF-Myc. Immunodetection with SecDF-specific antibodies showed that the SecDF-Myc protein was highly overproduced in xylose-induced cells of *B. subtilis* XDF-Myc, as neither wild-type SecDF nor SecDF-Myc were detectable in uninduced cells. Judged from its mobility on SDS-PAGE, SecDF-Myc is a protein of about 82 kDa, which is in agreement with the sequence-based prediction.

EXAMPLE VII

Detection of Gram-positive Microorganisms

The following example describes the detection of gram-positive microorganism SecDF.

DNA derived from a gram-positive microorganism is prepared according to the methods disclosed in Current Protocols in Molecular Biology, Chap. 2 or 3. The nucleic acid is subjected to hybridization and/or PCR amplification with a probe or primer derived from SecDF. A preferred probe comprises the nucleic acid section containing conserved amino acid sequences.

The nucleic acid probe is labeled by combining 50 pmol of the nucleic acid and 250 mCi of [gamma $^{32}$P] adenosine triphosphate (Amersham, Chicago Ill.) and T4 polynucleotide kinase (DuPont NEN®, Boston Mass.). The labeled probe is purified with Sephadex G-25 super fine resin column (Pharmacia). A portion containing $10^7$ counts per minute of each is used in a typical membrane based hybridization analysis of nucleic acid sample of either genomic or cDNA origin.

The DNA sample which has been subjected to restriction endonuclease digestion is fractionated on a 0.7 percent agarose gel and transferred to nylon membranes (Nytran Plus, Schleicher & Schuell, Durham N.H.). Hybridization is carried out for 16 hours at 40 degrees C. To remove nonspecific signals, blots are sequentially washed at room temperature under increasingly stringent conditions up to 0.1×saline sodium citrate and 0.5% sodium dodecyl sulfate. The blots are exposed to film for several hours, the film developed and hybridization patterns are compared visually to detect polynucleotide homologs of *B.subtilis* SecDF. The homologs are subjected to confirmatory nucleic acid sequencing. Methods for nucleic acid sequencing are well known in the art. Conventional enzymatic methods employ DNA polymerase Klenow fragment, SEQUENASE® (US Biochemical Corp, Cleveland, Ohio) or Taq polymerase to extend DNA chains from an oligonucleotide primer annealed to the DNA template of interest.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated in their entirety.

What is claimed is:

1. A method for the secretion of a protein in a Bacillus microorganism comprising the steps of,
   a) introducing into a Bacillus host cell a polynucleotide encoding a fusion protein, wherein said polynucleotide comprises
      i) a nucleic acid encoding a gram-positive secretion factor as set forth in SEQ ID NO: 2, selected from the group consisting of SecD, SecF and SecDF;
      ii) a promoter functional in said Bacillus host cell; and
      iii) a nucleic acid encoding a heterologous or homologous protein; and
   b) culturing the Bacillus host cell under conditions suitable for expression of said fusion protein, wherein the heterologous or homologous protein is secreted by the Bacillus host cell into the culture media.

2. The method according to claim 1 further comprising recovering the heterologous or homologous protein from the culture media.

3. The method according to claim 1, wherein the protein of iii) is a heterologous protein.

4. The method according to claim 3, wherein the heterologous protein is selected from the group consisting of hormones, growth factors, and cytokines.

5. The method according to claim 3, wherein the heterologous protein is an enzyme.

6. The method according to claim 5, wherein said enzyme is selected from the group consisting of proteases, cellulases, amylases, carbohydrases, lipases, isomerases, transferases, kinases, and phosphatases.

7. The method according to claim 1, wherein the protein of iii) is a homologous protein.

8. The method according to claim 1, wherein the secretion factor is SecD.

9. The method according to claim 1, wherein the secretion factor is SecF.

10. The method according to claim 1, it wherein the secretion factor is SecDF.

11. The method according to claim 1, wherein the promoter is heterologous to the selected gram-positive secretion factor.

12. The method according to claim 1, wherein the promoter is a gram-positive secretion factor wild type promoter.

13. The method according to claim 1, wherein the host cell is selected from the group consisting of *B. subtilis, B. licheniformis, B. lentus, B. brevis, B. stearothermophilus, B. alkalophilus, B. amyloliquifaciens, B. coagulans, B. circulans, B. lautus* and *B. thuringiensis*.

14. A Bacillus expression vector comprising,
   (iii) a nucleic acid encoding a gram-positive secretion factor as set forth in SEQ ID NO: 2 selected from the group consisting of SecD, SecF and SecDF; and
   (iv) a functional gram-positive secretion factor wild-type promoter.

15. The Bacillus expression vector of claim 14, wherein said vector comprises multiple copies of the nucleic acid encoding the gram-positive secretion factor.

16. A Bacillus host cell transformed with the expression vector of claim 14, wherein said host cell expresses said secretion factor.

17. The Bacillus host cell of claim 16, wherein said host cell is a *B. subtilis* cell.

18. The Bacillus expression vector of claim 14, wherein the nucleic acid encoding the gram-positive secretion factor is the sequence set forth in SEQ ID NO: 1 selected from secD, secF and secDF.

19. The Bacillus expression vector of claim 14, wherein the secretion factor is SecD.

20. The Bacillus expression vector of claim 14, wherein the secretion factor is SecF.

21. The Bacillus expression vector of claim 14, wherein the secretion factor is SecDF.

22. The Bacillus expression vector of claim 14 further comprising a nucleic acid encoding a heterologous or homologous protein.

* * * * *